United States Patent
Sang et al.

(10) Patent No.: US 7,459,542 B2
(45) Date of Patent: Dec. 2, 2008

(54) SEPARATION OF ALBUMIN FROM PROTEIN SAMPLES

(75) Inventors: Qing-Xiang (Amy) Sang, Tallahassee, FL (US); Ziad Joseph Sahab, Tallahassee, FL (US)

(73) Assignee: Florida State University Research Foundation, Inc., Tallahassee, FL (US)

( * ) Notice: Subject to any disclaimer, the term of this patent is extended or adjusted under 35 U.S.C. 154(b) by 419 days.

(21) Appl. No.: 11/366,149

(22) Filed: Mar. 2, 2006

(65) Prior Publication Data

US 2006/0205928 A1 Sep. 14, 2006

Related U.S. Application Data

(60) Provisional application No. 60/660,384, filed on Mar. 10, 2005.

(51) Int. Cl.
*A23J 1/00* (2006.01)

(52) U.S. Cl. .................. 530/412; 530/416; 530/418

(58) Field of Classification Search ................. 530/412, 530/416, 418
See application file for complete search history.

(56) References Cited

U.S. PATENT DOCUMENTS

| | | | |
|---|---|---|---|
| 4,228,154 A | 10/1980 | Fisher et al. | |
| 5,250,662 A | 10/1993 | Chang | |
| 5,888,966 A | 3/1999 | Larsen et al. | |
| 6,489,447 B1 | 12/2002 | Basey et al. | |

OTHER PUBLICATIONS

Ziad J Sahab and Qing-Xiang A Sang, Albumin elimination from human plasma, Abstract, Division of Analytical Chemistry, Aug. 28-Sep. 1, 2005, ANYL 150, Washington, DC.

Ben Herbert, Pier Giorgio Righetti, A Turning point in proteome analysis: Sample prefractionation via multicompartment electrolyzers with isoelectric membranes, Electrophoresis, 3639-3648, 21, Wiley-VCH Veriag GmbH, 69451 Weinheim, 2000.

Radhakrishna S. Tirumalai, King C. Chan, Darue A. Prieto, Haleem J. Issaq, Thomas P. Conrads, and Timothy D. Veenstrat, Characterization of the Low Molecular Weight Human Serum Proteome, pp. 1096-1103, Molecular & Cellular Proteomics 2.10, Aug. 13, 2003.

Stanford Moore and William H. Stein, Chromatography of Amino Acids on Sulfonated Polystyrene Resins, Journal of Biological Chemistry, Oct. 1951;192(2) pp. 663-681.

2-D Electrophoresis for Proteomics, A Methods and Product Manual, BIO-RAD Laboratories, Inc., Bulletin 2651 US/EG Rev C.

Ziad J Sahab, Yewseok Suh, and Qing-Xiang A Sang, Pre-fractionation of proteins from crude biological samples prior to 2-D gel electrophoresis, Abstract, Division of Analytical Chemistry, Aug. 28-Sep. 1, 2005, ANYL 151, Washington, DC.

Lian Shan and David J. Anderson, Gradient Chromatofocusing. Versatile pH Gradient Separation of Proteins in Ion-Exchange HPLC: Characterization Studies, Analytical Chemistry, American Chemical Society, vol. 74, No. 21, Nov. 1, 2002, pp. 5641-5649.

Ziad J. Sahab, Yewseok Suh, and Qing-Xiang Amy Sang, Isoelectric Point-Based Prefractionation of Proteins from Crude Biological Samples Prior to Two-Dimensional Gel Electrophoresis, Journal of Proteome Research, American Chemical Society, 2005, 4, pp. 2266-2272.

*Primary Examiner*—Tekchand Saidha
(74) *Attorney, Agent, or Firm*—Bryan Cave, LLP

(57) ABSTRACT

The present invention generally relates to methods for separating albumin from samples comprising albumin and other proteins based on the pI of albumin. More particularly, the methods relate to forming an aqueous combination comprising the sample and an anion or a cation exchange material at various pHs, agitating the combination, and separating a fraction of unbound proteins from a concentrated solids fraction comprising the ion exchange material and bound proteins.

35 Claims, 21 Drawing Sheets

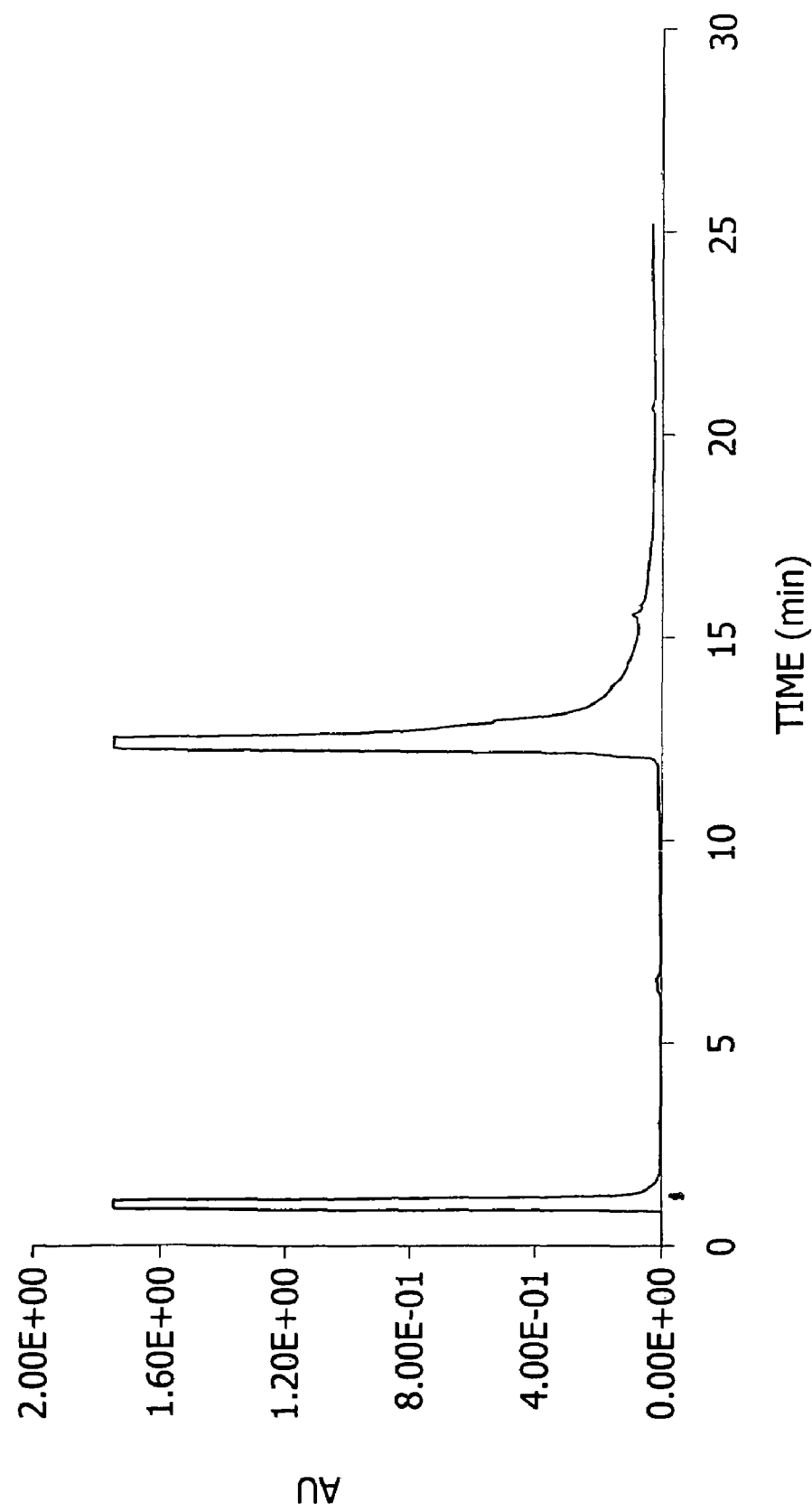

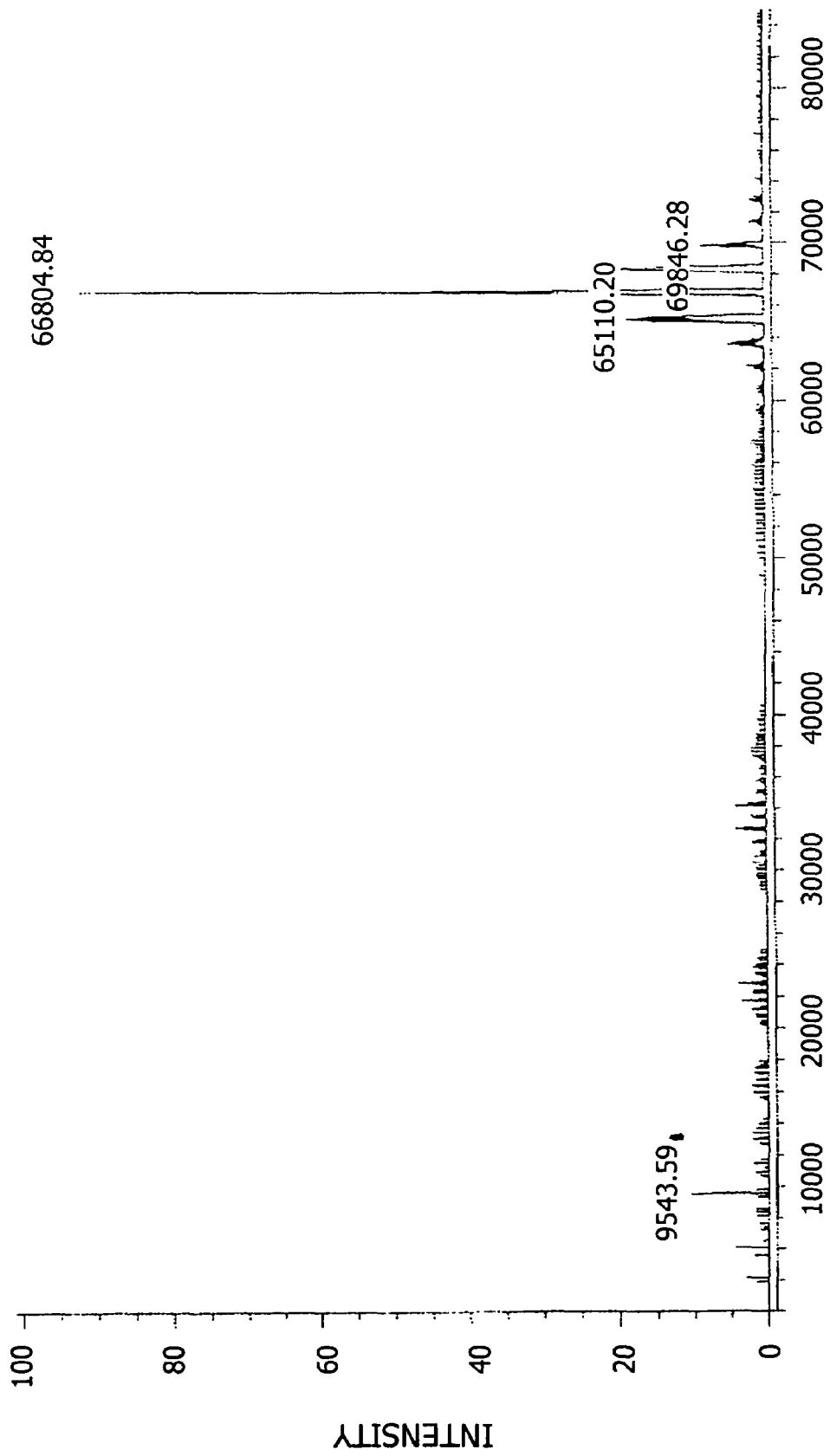

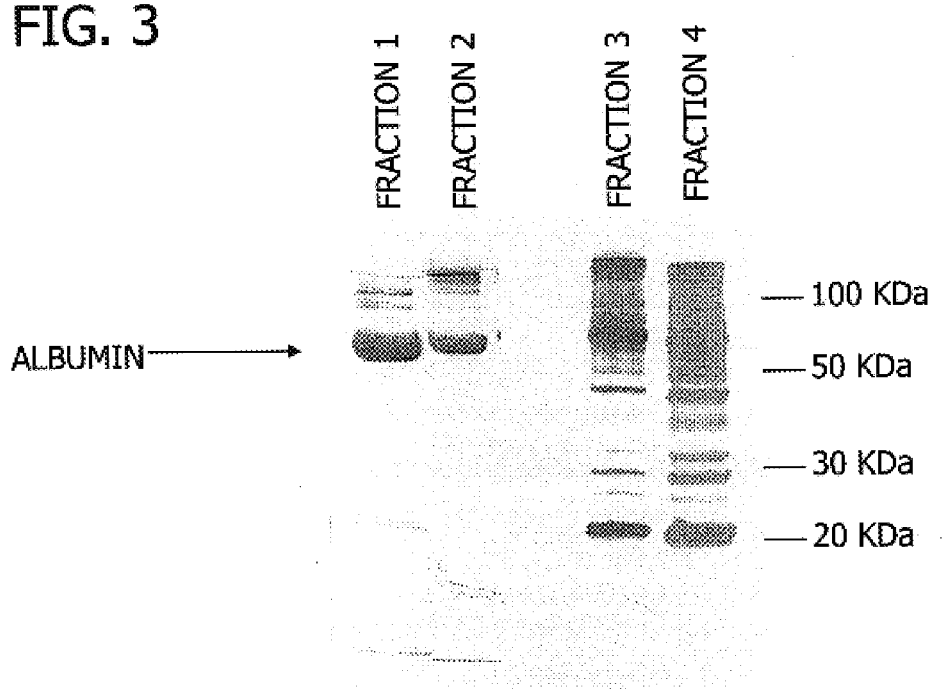

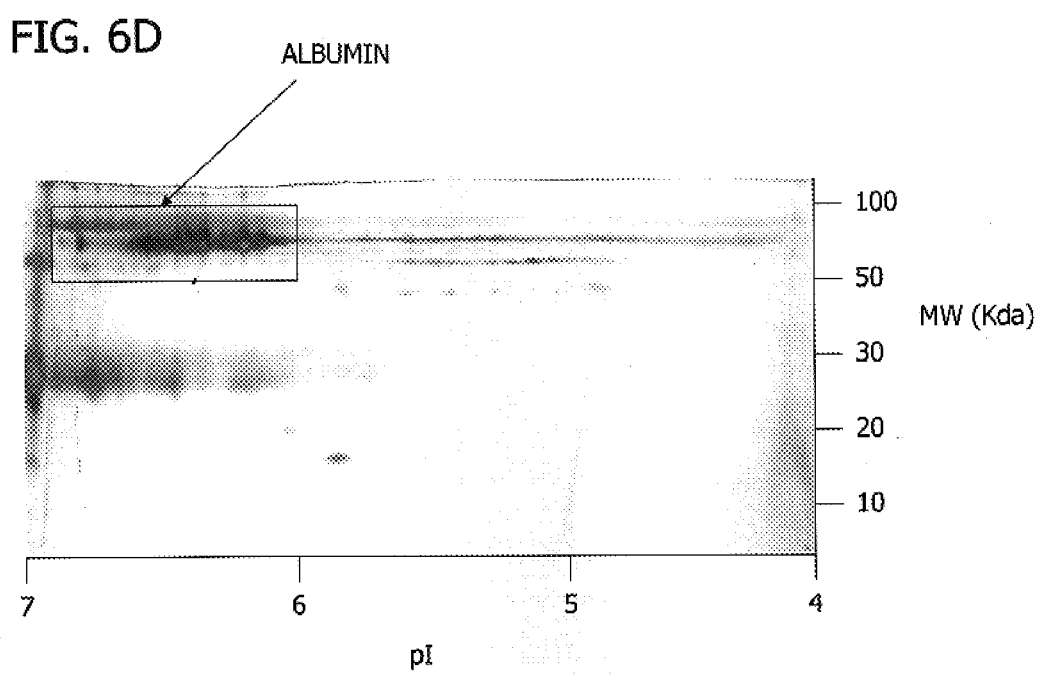

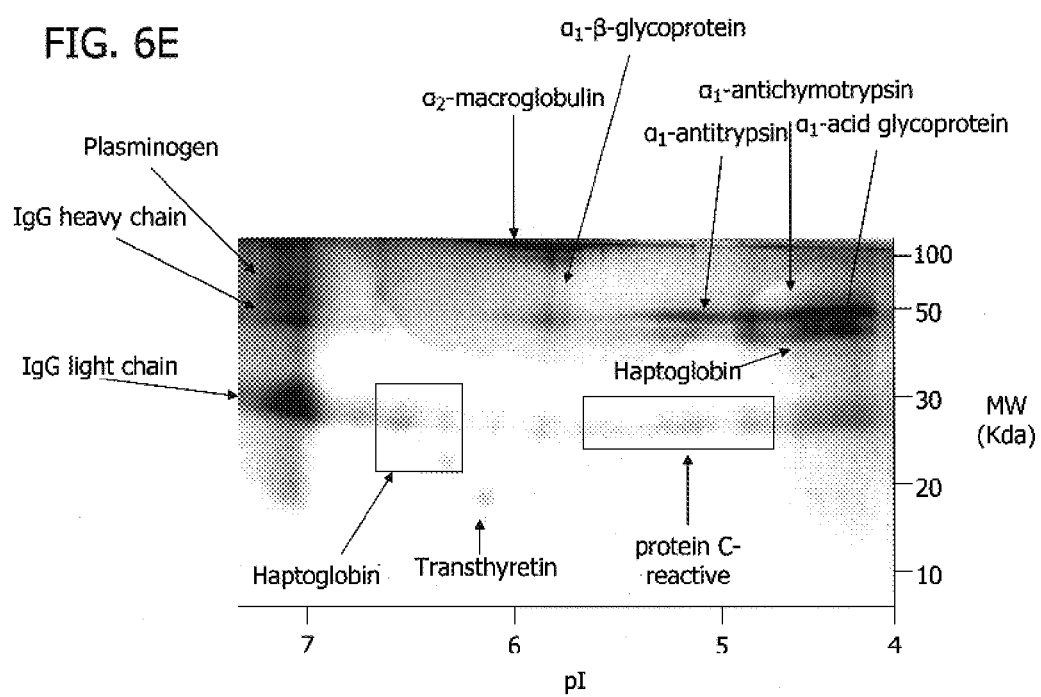

SEPARATION OF ALBUMIN FROM PROTEIN SAMPLES

REFERENCE TO RELATED APPLICATION

This is a non-provisional application claiming priority under 35 U.S.C. § 119 to provisional application No. 60/660, 384, filed Mar. 10, 2005, the entire contents of which are incorporated herein by reference.

FIELD OF THE INVENTION

The present invention generally relates to methods for separating albumin from samples comprising albumin and other proteins based on the pI of albumin. More particularly, the methods relate to forming an aqueous combination comprising the sample and an anion or a cation exchange resin at various pHs, agitating the combination, and separating a fraction of unbound proteins from a concentrated solids fraction comprising the ion exchange material and bound proteins.

BACKGROUND OF THE INVENTION

Albumin is found in a variety of biological samples, including plasma, amniotic fluid, seminal fluid, and cerebral spinal fluids, among others. Albumin is highly abundant in such samples, and in particular, constitutes more than 50% of total plasma proteins. Often, however, it is desirable to identify low abundance or low molecular weight proteins or peptides present in the sample, since such proteins or peptides may serve as important biomarkers for a variety of diseases, including cancer. Two-dimensional (2D) polyacrylamide gel electrophoresis is the preferred platform of large-scale protein microcharacterization, as it allows for qualitative and quantitative analysis of the proteome. However, the separation of low abundance proteins from plasma or serum samples by 2D gel is complicated by the high abundance of albumin present in human serum. In many cases this arises from limitations in protein loading on the isoelectric focusing gel (first dimension of the separation) using an Immobilized pH Gradient (IPG) strip. Therefore, by significantly depleting the amount of albumin present in a plasma sample, it is expected that visualization of the other plasma proteins will be improved, and increased total protein load will enable the detection of less abundant proteins.

In addition, albumin is known to bind to a variety of substances present in serum or plasma samples, including various peptides, proteins, protein fragments, hormones, cytokines, fatty acids, and other small molecular biomarkers that may contain important diagnostic information. Since albumin may bind to these biomarkers, these biomarkers are often eliminated from the biological sample along with the albumin by traditional separation and fractionation techniques. It would therefore be advantageous to be able to separate albumin from a biological sample, without simultaneously eliminating biomarkers that may be bound to the albumin.

Several techniques have been used for the elimination or reduction of albumin from serum samples. One such technique uses Cibacron blue dye. One example of a Cibacron blue-related method uses a crosslinked agarose bead with covalently attached Cibacron blue F3GA dye (Affi-Gel Blue, Bio-Rad, Hercules, Calif.). The attached dye functions as an ionic, hydrophobic, aromatic, and sterically active binding site for proteins. Other reports indicate that Cibacron Blue F3GA dye has a specific affinity to most proteins that contain a dinucleotide fold, therefore mimicking nicotinamide adenine dinucleotide and other purine dinucleotides. However, given the multiple functions of the attached dye, the total removal of albumin using the Affi-Gel Blue method will not only clear albumin and many proteins with the same isoelectric point (pI), but also the proteins that can bind to the planar ring structure of Cibacron Blue F3GA dye through a complex combination of electrostatic, hydrophobic and hydrogen-bonding interactions. For example, biomolecules such as interferon, lipoproteins, hemopexin, antithrombin II, blood coagulation factors, nicotinamide adenine dinucleotide, and other purin dinucleotides may also be bound. Thus, because of the multiple dye interactions and binding of non-albumin proteins and other molecules, methods based on the use of the Cibacron blue dye only provide a partial separation of albumin from other proteins.

Isoelectric trapping and Gradiflow™ separation have also been used for the elimination of albumin from a sample. Isoelectric trapping uses multicompartment electrolyzers with isoelectric membranes. This device acts to purify proteins to homogeneity in a liquid vein by capturing them in an isoelectric trap formed by two immobiline membranes with pIs encompassing the pI of the species under analysis. Gradiflow™ separation is capable of separating proteins on the basis of their molecular weight and charge by selection of a specific separation membrane cutoff size and adjusting the pH of the system. These techniques, however, have several disadvantages including the high cost of the instrumentation and the frequent maintenance, the lengthy treatment time of the serum sample, and the loss of several plasma proteins during processing, including proteins with a pI the same as or close to that of albumin. In addition, the conditions under which isoelectric trapping is performed may result in the denaturing of proteins in the sample, rendering these proteins unsuitable for further examination.

Other techniques have utilized antibodies which bind albumin as the albumin containing sample passes through a column. Although such techniques provide for relatively good separation of albumin from other proteins present in the sample, some cross reactivity with other proteins may occur. In addition, the antibodies used in such techniques are not always stable (i.e., they may be denatured by running conditions or digested by proteinases present in plasma samples), and the cost may be prohibitive.

SUMMARY OF THE INVENTION

The present invention provides a novel method for the separation of albumin from samples comprising albumin and other proteins, with minimal loss of the remaining proteins. This method uses common instrumentation, can be quickly performed, and is carried out in non-denaturing conditions, making the remaining proteins suitable for further structural, chemical, and biological analysis. In one embodiment the procedure takes fewer than about 30 minutes. In addition, the methods of the present invention not only enable proteins that have a pI close to that of albumin to be recovered, but also some proteins having a pI that falls into the same pI range as albumin may be recovered. As a result, less abundant proteins that are usually bound to albumin or masked by the presence of albumin may be detected. A further advantage of removing albumin is an increase detection level of all non-albumin proteins in the sample because of their increased concentration in the purified sample. In addition, the separation of albumin from other proteins in the biological sample provides a purer sample of albumin, which may then be used in other applications or further purified. The total protein recovery is increased because the albumin is separated in a usable form, not consumed by the process of its elimination.

In one embodiment, the present invention provides a method for separating albumin from a sample comprising albumin and other proteins. The method comprises combining the sample with an anion exchange material to form a first aqueous combination, the pH of the first aqueous combination being a pH at which albumin precipitates from the first aqueous combination; agitating the first aqueous combination to induce the albumin and proteins having a pI less than the pH of the first aqueous combination to precipitate from the aqueous combination or to bind to the anion exchange material; and separating the anion exchange material from the agitated aqueous combination.

Also provided is a method for separating albumin from a sample comprising albumin and other proteins. The method comprises forming a first aqueous dispersion, the first aqueous dispersion comprising the sample and a particulate anion exchange resin at a pH of about 5.9, wherein the resin is capable of free-flowing movement relative to the rest of the dispersion; agitating the first aqueous dispersion to induce the albumin and proteins having a pI less than about 5.9 to precipitate from the aqueous dispersion or to bind to the anion exchange resin; centrifuging the agitated first aqueous dispersion to form a first supernatant fraction and a first concentrated solids fraction, the first concentrated solids fraction comprising the precipitate and the anion exchange resin; separating the first supernatant from the first concentrated solids fraction; forming a second aqueous dispersion, the second aqueous dispersion comprising the separated first concentrated solids fraction at a pH of about 4.9; agitating the second aqueous dispersion; centrifuging the agitated second aqueous dispersion to form a second supernatant fraction and a second concentrated solids fraction, the second concentrated solids fraction comprising the anion exchange resin; separating the second supernatant from the second concentrated solids fraction; forming a third aqueous dispersion, the third aqueous dispersion comprising the separated second concentrated solids fraction at a pH of about 3.3; agitating the third aqueous dispersion; centrifuging the agitated third aqueous dispersion to form a third supernatant fraction and a third concentrated solids fraction, the third concentrated solids fraction comprising the anion exchange resin; separating the third supernatant from the third concentrated solids fraction; forming a fourth aqueous dispersion, the fourth aqueous dispersion comprising the separated third concentrated solids fraction at a pH of about 1.0; agitating the fourth aqueous dispersion; centrifuging the agitated fourth aqueous dispersion to form a fourth supernatant fraction and a fourth concentrated solids fraction, the fourth concentrated solids fraction comprising the anion exchange resin; and separating the fourth supernatant from the fourth concentrated solids fraction.

The present invention also provides a method for separating albumin from a sample comprising albumin and other proteins. The method comprises combining the sample with a cation exchange material to form a first aqueous combination, the pH of the first aqueous combination being a pH at which albumin precipitates from the first aqueous combination; agitating the first aqueous combination to induce the albumin and proteins having a pI greater than the pH of the first aqueous combination to precipitate from the aqueous combination or to bind to the cation exchange material; and separating the cation exchange material from the agitated aqueous combination.

Also provided is a method for separating albumin from a sample comprising albumin and other proteins. The method comprises forming a first aqueous dispersion, the first aqueous dispersion comprising the sample and a particulate cation exchange resin at a pH of about 5.9, wherein the resin is capable of free-flowing movement relative to the rest of the dispersion; agitating the first aqueous dispersion to induce the albumin and proteins having a pI greater than about 5.9 to precipitate from the aqueous dispersion or to bind to the cation exchange resin; centrifuging the agitated first aqueous dispersion to form a first supernatant fraction and a first concentrated solids fraction, the first concentrated solids fraction comprising the precipitate and the cation exchange resin; separating the first supernatant from the first concentrated solids fraction; forming a second aqueous dispersion, the second aqueous dispersion comprising the separated first concentrated solids fraction at a pH of about 6.9; agitating the second aqueous dispersion; centrifuging the agitated second aqueous dispersion to form a second supernatant fraction and a second concentrated solids fraction, the second concentrated solids fraction comprising the cation exchange resin; separating the second supernatant from the second concentrated solids fraction; forming a third aqueous dispersion, the third aqueous dispersion comprising the separated second concentrated solids fraction at a pH of about 8.0; agitating the third aqueous dispersion; centrifuging the agitated third aqueous dispersion to form a third supernatant fraction and a third concentrated solids fraction, the third concentrated solids fraction comprising the cation exchange resin; separating the third supernatant from the third concentrated solids fraction; forming a fourth aqueous dispersion, the fourth aqueous dispersion comprising the separated third concentrated solids fraction at a pH of about 14.0; agitating the fourth aqueous dispersion; centrifuging the agitated fourth aqueous dispersion to form a fourth supernatant fraction and a fourth concentrated solids fraction, the fourth concentrated solids fraction comprising the cation exchange resin; and separating the fourth supernatant from the fourth concentrated solids fraction.

Additionally, the present invention provides a method for separating albumin from a sample comprising albumin and other proteins. The method comprises combining the sample with an ion exchange material to form a first aqueous combination, the pH of the first aqueous combination being (i) less than the pI of a first fraction of the proteins in the first aqueous combination, (ii) greater than the pI of a second fraction of the proteins in the first aqueous combination, and (iii) a pH at which albumin precipitates from the first aqueous combination; agitating the first aqueous combination to induce the albumin to precipitate and to cause protein comprised by one of said first and second fractions to bind to the ion exchange material; and separating the ion exchange material from the agitated aqueous combination.

BRIEF DESCRIPTION OF THE DRAWINGS

FIG. 2 depicts the results of nonporous silica-reverse phase-HPLC-electrospray ionization-time of flight-mass spectrometry (i.e., NPS-RP-HPLC-ESI-TOF-MS), as described in Example 1. FIG. 2A is the NPS-RP-HPLC chromatogram of fractions 1 and 2 from FIG. 1. 10 µL of each fraction was injected. The first peak (i.e., at approximately 1 minute) is the salt ions, and the second peak (i.e., at approximately 12.5 minutes) is albumin. FIG. 2C is the deconvolution of the measured spectrum. The deconvolution parameters are: threshold 10% and resolution 1 Da.

FIG. 3 depicts the separation by 12% SDS polyacrylamide gels of fractions 1 to 4 from the chromatogram shown in FIG. 1, as described in Example 1. The gels of the highly concentrated fractions 1 and 2 were stained by coomassie blue. The gels for fractions 3 and 4, having a lower concentration, were silver stained.

FIG. 4C and FIG. 4D are computer enhanced to give a clearer image.

FIG. 5C and FIG. 5D are computer enhanced to give a clearer image.

FIG. 6A-FIG. 6E depict the 2-DE of the original sample and samples fractionated in Example 1. FIG. 6A depicts the original 100 µg human plasma protein sample before the albumin elimination procedure. FIG. 6B depicts the combined 8 fractions collected after the 75% B and pH1 washes. FIG. 6C depicts the combined 4 fractions collected after the 90% B washes. FIG. 6D depicts the original 275 µg human plasma protein sample before the albumin elimination procedure. FIG. 6E depicts the combined 8 fractions collected after the 75% B and pH1 washes. The IPG strips used are 11 cm long, pH 4 to 7. The 10% gels used for SDS-PAGE in the second dimension of separation were silver stained. The pI range is shown at the bottom of the gels. The molecular masses (kDa) are labeled on the left of the gels.

DETAILED DESCRIPTION OF THE INVENTION

Figure 1:
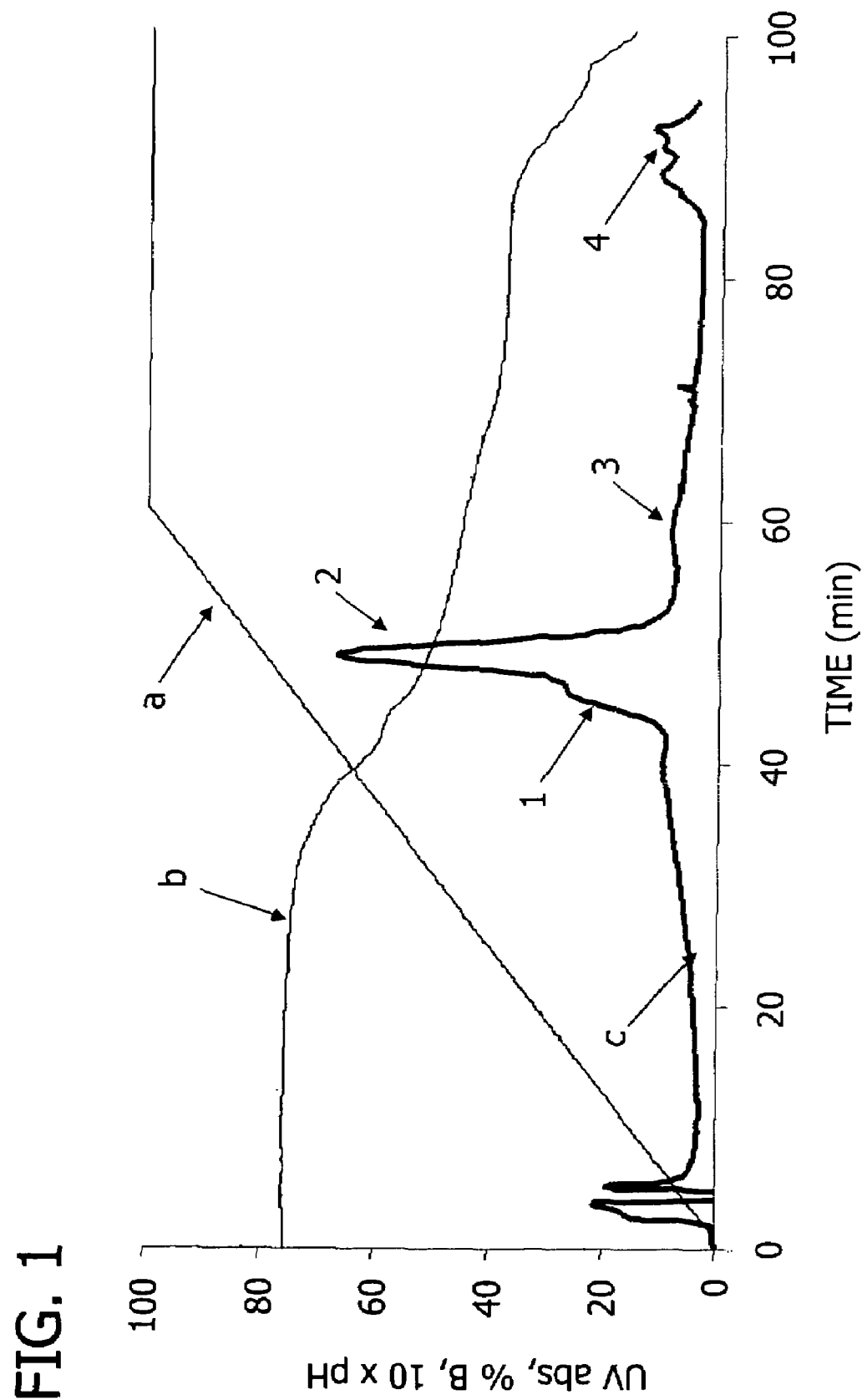
FIG. 1 depicts a chromatogram of the chromatofocusing separation of 1.355 mg contained in 22.5 µL of a human plasma protein sample, as described in Example 1. (a) is the concentration of the elution buffer (i.e., buffer B) set from 0 to 100% in 60 minutes; (b) is the pH gradient generated by the mixing of buffer A (pH=8) and buffer B (pH=3.3); and (c) is 215 nm absorption of the eluting plasma proteins for fractions 1 to 4. Fractions 1 to 4 represent the different fractions that were collected and analyzed by liquid chromatography mass spectrometry and SDS-polyacrylamide gel.

The present invention relates to methods for separating albumin from a sample comprising albumin and other proteins. More specifically, a method is provided wherein albumin is separated from a biological sample, such as a plasma sample, by adjusting the pH of the sample based on the theoretical pI of albumin. The methods may be performed using either an anion or cation exchange resin.

The methods described herein have broad application, including: separating a fraction of proteins with a pI below that of albumin from a sample comprising albumin and other proteins; separating a fraction of proteins with a pI above that of albumin from a sample comprising albumin and other proteins; separating proteins with a specific pI from a mixture of proteins including albumin; and separating an albumin fraction from a sample comprising albumin and other proteins.

Proteins are amphoteric molecules that can carry a positive, negative, or zero net charge depending on the pH of their local environment and the isoelectric point (pi) of the protein. The tendency of a protein to bind to an ion exchange resin, whether an anion or cation exchange resin, can thus be manipulated by adjusting the pH of the protein's local environment.

For every protein, there is a pH at which its net charge is zero. This pH value is the pI of the protein. The pI values for different proteins vary over the pH spectrum. By adjusting the pH of a sample comprising the desired protein, the charge on a particular protein can be manipulated, and used to separate that particular protein from other proteins present in the sample.

For example, when the pH of the sample is equal to the theoretical pI of a particular protein, the net charge on the protein is zero, and the protein will not bind to either an anion or cation exchange material. Many proteins, including albumin, are relatively insoluble at pH values that approach the protein's pI value; unless a protein has a relatively high solubility, it will typically precipitate from aqueous solutions having a pH within 0.5 pH units of the protein's pI value. Thus, for example, albumin tends to precipitate from solutions having a pH value approximately equal to its pI.

Binding of proteins to a cation or anion exchange material can likewise be induced by adjusting the pH of the sample relative to the pI of the desired protein. For example, when the pH of a sample is adjusted to a pH below the pI of a particular protein, that protein (and all proteins with a pI greater than the pH of the sample) will have a net positive charge, and will bind to a cation exchange material but will have little or no affinity for an anion exchange material. The strength of the binding to the cation material will depend on the total charge of the protein. Thus, for example, if the pI of the protein is far above the pH of the sample, the protein will have a larger positive charge, and the binding to a cation exchange material will be strong; if the pI of the protein is only slightly above the pH of the sample, the protein will have a weaker positive charge, and the binding to a cation exchange material will be relatively weak. Conversely, when the pH of a sample is adjusted to a pH above the pI of a particular protein, that protein (and all proteins with a pI below the pH of the sample) will have a net negative charge, and will bind to an anion exchange material but will have little or no affinity for a cation exchange material. Again, the strength of the binding to the anion exchange material will depend on the total charge of the protein, and may be adjusted by increasing or decreasing the pH of the sample.

In the methods of the present invention, these principles are employed to aid in the separation of albumin from a sample comprising albumin and other proteins, peptides, amino acids, and/or other charged molecules. Albumin may be found in a variety of biological samples, including plasma or serum samples, amniotic fluid, seminal fluid, and cerebral spinal fluids, among others. As discussed above, in some instances it may be desirable to eliminate albumin from the biological sample containing albumin in order to increase the resolution and visualization of other proteins present in the sample, which may otherwise be masked by the presence of albumin. In other instances, it may be desirable to separate a fraction of proteins with a specific pI or pI range from a biological sample containing albumin, or alternately, to separate an albumin fraction from the biological sample for further processing of the albumin. The albumin fraction can be further investigated to detect and identify the albumin-bound peptides, proteins, fatty acids, drugs, and other biomolecules that may contain specific biomarkers for different disease states and other medical conditions. The fraction of albumin collected can also be used for therapeutic purposes after further purification since in the present invention albumin is not denatured by organic solvents. The present invention provides methods for accomplishing these separations by using a quick, efficient, and low cost procedure.

For instance, a fraction of proteins with a pI greater than that of albumin may be separated from a sample comprising albumin and other proteins, a fraction of proteins with a pI less than that of albumin may be separated from the sample, and/or an albumin fraction may be separated from the sample. In addition, proteins with a specific pI or proteins that have a pI within a specific pI range may be isolated from the sample, by using a stepwise fractionation technique. These separations may be performed using either an anion or a cation exchange resin. Although any of the above described separations may be performed using either an anion or cation exchange resin, it may be preferable to use one type of resin over the other, depending on the separation to be performed.

For example, in a first step, the aqueous sample comprising albumin and other proteins is combined with an ion exchange material to form an (a first) aqueous combination at a (first) pH. If cation exchange material is used, in a second step, agitation of the combination causes (i) protein(s) having a pI greater than the pH of the combination to bind to the cation exchange resin, (ii) protein(s) having a pI value approximately equal to the pH of the combination to precipitate, and (iii) protein(s) having a pI less than the pH of the combination to remain dissolved in the aqueous solution. Alternately, if anion exchange material is used in a second step, agitating the combination causes (i) protein(s) having a pI less than the pH of the combination to bind to the anion exchange resin, (ii) protein(s) having a pI value approximately equal to the pH of the combination to precipitate, and (iii) protein(s) having a pI greater than the pH of the combination to remain dissolved in the aqueous solution. After agitating is complete and protein(s) is/are bound to the ion exchange material, the combination is separated in a third step into a concentrated solids fraction (containing the ion exchange material and any precipitate) and an aqueous (supernatant) fraction; for example, the ion exchange material may simply be filtered or centrifuged from the combination. In a fourth step, the protein(s) of interest (whether in the concentrated solids fraction or aqueous fraction) is/are recovered and optionally used as-is or subjected to further purification. If the proteins of interest are in the solids fraction (as a precipitate or a species bound to the ion exchange resin), the recovery step preferably includes re-dissolving the protein(s) of interest after the solids fraction has been separated from the liquid fraction. Thus, for example, in the recovery step the solids fraction may be combined with an aqueous solution, preferably a buffered solution, having (i) a pH up to about 1 pH unit greater than the pI of the protein of interest when the ion exchange resin is cation exchange resin or (ii) a pH up to about 1 pH unit less than the pI of the protein of interest when the ion exchange resin is anion exchange resin.

If further purification is desired, the separation steps (steps 1-4) may be repeated, but in the second iteration of these steps, a (second) aqueous combination is prepared by combining the concentrated solids fraction or the liquid fraction derived from the prior (first) iteration of the steps with a pH adjusting agent or optionally an ion exchange material (which may be the same or different, even a different type than that used in the previous iteration) at a (second) pH wherein the second pH differs from the first pH. In this manner, the protein(s) obtained in the concentrated solids fraction or the liquid fraction from the first iteration of steps 1-4 may be further fractionated based upon the pI of the protein(s) in the fraction. Extending this approach, if further purification is desired, steps 1-4 may be repeated, but in the third and each successive iteration of these steps, a (third and successive) aqueous combination is prepared by combining the concentrated solids fraction or the liquid fraction derived from the prior iteration of the steps with a pH adjusting agent or optionally an ion exchange material (which may be the same or different, even a different type than that used in the previous iteration) at a (third and successive) pH in step 1 wherein each successive pH differs from the previous pH.

In a preferred embodiment, whether an anion or cation exchange material is used, the pH of the aqueous combination is selected so that the albumin present in the sample precipitates during the initial separation. For example, if proteins with a pI greater than that of albumin are to be separated from the sample, it may be advantageous to perform the separation using an anion exchange material at a pH wherein albumin precipitates and proteins with a pI less than the pI of albumin are bound to the anion exchange material, as described below. Under these conditions, the soluble, unbound proteins comprise the proteins with a pI greater than that of albumin, and these proteins can be readily separated from the precipitated albumin and anion exchange material. The albumin may then be redissolved and recovered and/or the bound proteins (having a pI less than that of albumin) released from the anion exchange material and recovered by adjusting the pH at which the separation occurs. Alternately, proteins with a pI less than that of albumin may advantageously be separated from the sample by performing the separation using a cation exchange resin at a pH wherein albumin precipitates and proteins with a pI greater than that of albumin are bound to the cation exchange material. Under these conditions, the soluble, unbound proteins comprise the proteins with a pI less than that of albumin, and these proteins can be readily separated from the cation exchange material. The albumin may then be redissolved and recovered and/or the bound proteins (having a pI greater than that of albumin) may be released from the cation exchange material and recovered by adjusting the pH at which the separation occurs.

In an alternate embodiment, whether an anion or cation exchange material is used, the pH of the aqueous combination may be selected so that the albumin present in the sample remains in the aqueous (supernatant) fraction during the initial separation. For example, proteins with a pI greater than that of albumin may be separated from the sample using a cation exchange material at a pH wherein albumin remains soluble and proteins with a pI greater than albumin are bound to the cation exchange material. A suitable pH may be, for example, greater than about 5.9, typically about 5.9 to about 5.9, and preferably is about 6.9. Under these conditions, the aqueous fraction comprises albumin and proteins with a pI less than the pH of the combination (including proteins with a pI less than that of albumin). These proteins can be readily separated from the cation exchange material, using the methods described herein. The proteins bound to the cation exchange material (including proteins having a pI greater than albumin) may then be released from the cation exchange material and recovered in a second separation by increasing the pH at which the separation occurs. The albumin may also be separated and recovered from the aqueous fraction by (i) decreasing the pH of the soluble fraction to a pH at which albumin precipitates and recovering the precipitated albumin. This may be done by, for example, decreasing the pH of the aqueous fraction to a pH of less than about 6.9, typically about 6.9 to about 4.9, and preferably to a pH of about 5.9. Alternately, the albumin may be separated and recovered from the aqueous fraction by (ii) combining the aqueous fraction with additional ion exchange material (whether anion or cation exchange material) to form a second aqueous combination, and adjusting the pH of the second aqueous combination so that the (a) the albumin binds to the ion exchange material or precipitates, and (b) the proteins with a pI less than albumin remain in the aqueous fraction or bind to the ion exchange material. In another example, proteins with a pI less than that of albumin may be separated from the sample using an anion exchange material at a pH wherein albumin remains soluble and proteins with a pI less than albumin are bound to the anion exchange material. A suitable pH may be, for example less than about 5.9, typically about 5.9 to about 4.9, and preferably is about 4.9. Under these conditions, the aqueous fraction comprises albumin and proteins with a pI greater than the pH of the combination (including proteins with a pI greater than that of albumin). These proteins can be readily separated from the anion exchange material using the methods described herein. The proteins bound to the anion exchange material (including proteins having a pI less than albumin) may then be released from the anion exchange material and recovered in a second separation by decreasing the pH at which the separation occurs. The albumin may also be separated and recovered from the soluble fraction by (i) increasing the pH of the soluble fraction so that the albumin precipitates, and recovering the precipitated albumin. This may be done by, for example, increasing the pH of the aqueous fraction to a pH of greater than about 4.9, typically about 4.9 to about 6.9, and preferably to a pH of about 5.9. Alternately, the albumin may be separated and recovered from the aqueous fraction by (ii) combining the aqueous fraction with additional ion exchange material (whether anion or cation exchange material) to form a second aqueous combination, and adjusting the pH of the second aqueous combination so that (a) the albumin binds to the ion exchange material or precipitates, and (b) the proteins with a pI greater than albumin remain in the aqueous fraction or bind to the ion exchange material.

In yet another alternative, it may be desirable to isolate an albumin fraction from other proteins in the sample. In this instance, either an anion or a cation exchange resin may advantageously be used, as described herein. The fraction of the sample recovered thus will vary depending on the pH at which the separation occurs, and the choice of resin. These and other separations are described more fully below.

In one alternative embodiment, the sequence of separation steps are carried out using both cation and anion exchange material. Because the two have an affinity for each other, it is preferred that contact between the two be minimized. Thus, for example, the aqueous combination is at a pH which induces (i) protein(s) having a pI greater than the pH of the combination to bind to the cation exchange material, (ii) protein(s) having a pI value approximately equal to the pH of the combination to precipitate, and (iii) protein(s) having a pI less than the pH of the combination to bind to the anion exchange material. By selecting a buffer having a desired pH (e.g., a pH at which albumin precipitates), therefore, proteins whether in the form of a precipitate (e.g., albumin) or bound to the cation or anion exchange material may be selectively re-dissolved into an aqueous solution and thus separated from the other proteins. By selecting multiple buffers (or pH's), a series of proteins may be selectively re-dissolved, thus effectively fractionating the original protein mixture into a plurality of products. To minimize contact between the anion and cation exchange materials, the two may be in different formats (e.g., one in the form of a particulate resin and the other in the form of a membrane or other non-particulate form) or the two may be in the same form (e.g., each in particulate form) but some measure (e.g., a membrane or other physical barrier) is used to minimize contact between the anion and cation exchange materials. Preferably, contact between the cation and anion exchange material is avoided.

Although a range of conventional ion exchange materials are commercially available and compatible with the process of the present invention, it is generally preferred that the ion exchange material be in the form a particulate ion exchange resin. In this embodiment, the aqueous combination may alternatively be referred to as an aqueous dispersion (i.e., a dispersion of resin particles in an aqueous solution) and, this terminology is used elsewhere herein to describe this preferred embodiment. Having the ion exchange material in particulate form readily facilitates agitation. That is, the agitation step may be carried out using any suitable means, as discussed below, including a vortex or magnetic stirrer operated at a sufficient speed (revolutions per minute, "rpm") to cause a vortex to form in the liquid. Preferably, the cavity in the center of the swirling liquid extends at least 50%, preferably at least 75%, still more preferably at least 90%, and still more preferably at least 99% of the distance from the surface of the liquid to the bottom of the container.

Separation Using an Anion Exchange Resin

In certain embodiments, separation is performed using an anion exchange resin. An anion exchange material may be used to perform a variety of separations, including: (i) separating a fraction of proteins with a pI greater than that of albumin from a sample comprising albumin and other proteins; (ii) separating an albumin fraction from a sample comprising albumin and other proteins; (iii) separating a fraction of proteins with a pI less than that of albumin from a sample comprising albumin and other proteins; and (iv) separating proteins with a pI less than that of albumin into fractions based on their pI. Separation (i) is especially efficient when an anion exchange resin is used.

Separating Proteins with a pI Greater than Albumin from a Sample

When using an anion exchange material, the initial separation is preferably performed at a pH wherein albumin will precipitate. Preferably, this pH is the theoretical pI of albumin. As discussed above, the pI value of a protein is the point at which its net charge is zero. Although the theoretical pI of albumin is approximately 5.92, the actual pI for various albumin molecules may vary slightly depending on the degree of glycosylation of the albumin. Thus, while most albumin will precipitate at pH 5.9 (the theoretical pI of albumin), some albumin may still have a slight positive or negative charge at this pH.

Therefore, in one embodiment, the present invention provides a method for separating albumin from a sample comprising albumin and other proteins using an anion exchange material. The method comprises combining the aqueous sample with anion exchange material to form a first aqueous combination, the first aqueous combination comprising the sample (comprising albumin and other proteins) and an anion exchange material. Preferably, the anion exchange material is in the form of a particulate resin and the aqueous combination is an aqueous dispersion of the particulate resin in the sample. Preferably, the anion exchange resin is capable of free-flowing movement relative to the rest of the dispersion, as discussed below, and is advantageously first equilibrated to the pH of the first aqueous dispersion prior to performing the separation. Alternately, instead of a free-flowing, particulate resin, the anion exchangers may be coated onto the interior surface or a portion of the interior surface of the container in which the separation is being performed, or may be present in other forms, such as described below. In this instance, the aqueous combination would comprise the sample (comprising albumin and other proteins) in contact with the anion exchangers, but would not necessarily be an aqueous dispersion.

This first aqueous dispersion is preferably formed at a pH at which albumin precipitates from the aqueous dispersion. As previously discussed, this pH is typically about 5.9, but may vary slightly depending on the degree of glycosylation of the albumin. Alternately, the first aqueous dispersion is formed at a pH at which albumin does not precipitate or bind to the anion exchange resin, but proteins with a pI less than the pH of the dispersion (including proteins with a pI less than albumin) bind to the anion exchange material. In one embodiment, this pH is less than about 5.9, typically about 5.9 to about 4.9, and preferably is about 4.9.

The first aqueous dispersion may also be agitated. As previously discussed, albumin present in a biological sample may sometimes be bound to various other proteins and biomarkers also present in the sample. Agitation helps reduce the amount of non-specific binding of albumin to other proteins present in the sample, and thus may increase the amount of these proteins recovered during the separation. Agitation also increases the contact probability between the ion exchangers and the proteins, and allows for more uniform distribution of any added buffer or agent used to adjust pH and therefore more uniform pH in every area of the dispersion. Thus, agitation helps induce the albumin and proteins with a pI less than the pH of the first aqueous dispersion to precipitate and/or bind to the anion exchange resin. Agitation may be done by any method known in the art, including shaking, stirring, mixing, and vortexing, among others. Preferably, the aqueous dispersion is agitated sufficiently to result in turbulent flow of the sample over the ion exchangers. This is particularly preferred when the ion exchangers are in a form other than a free-flowing particulate resin.

It will be recognized that the degree of separation is dependent on the intensity of agitation as well as time. For example, if the aqueous dispersion is only gently agitated, it will be necessary to agitate the mixture for a longer period of time in order to obtain a comparable degree of separation as would be obtained were the aqueous dispersion agitated vigorously for a shorter period of time. Agitation may thus range from gentle agitation to intensely mixing. In general, more vigorous agitation will decrease the time required to obtain the desired degree of separation. Since more vigorous agitation decreases the time required to obtain the desired degree of separation, it is generally preferred that the agitation be done by intensely mixing the aqueous dispersion, for example by vortexing, using an orbital shaker (e.g., flat, rotating, vertical shakers, etc.), or by vigorous hand shaking. Preferably, the intense mixing is done by vortexing. When the aqueous dispersion is vortexed, the vortexing may be done at any suitable speed, and preferably is done at a speed of at least about 200 rpm, more preferably at a speed of at least about 500 rpm, and still more preferably at a speed of at least about 1000 rpm. Typically, speeds in excess of about 5,000 rpm will not be employed with speeds in the range of about 800 rpm to about 1200 rpm being typical. There is generally no upper limit on the length of time the aqueous dispersion may be agitated. However, as previously discussed, the more vigorous the agitation, the less time the aqueous dispersion needs to be agitated. In one example, when the aqueous dispersion is agitated by vortexing, the aqueous dispersion is vortexed for about 10 seconds to several hundred seconds (e.g., about 300 seconds); typically, the aqueous dispersion will be vortexed for a period of about 20 to about 50 seconds. In one embodiment, the aqueous dispersion is vortexed at a speed of about 1000 rpm for about 30 seconds.

After the first aqueous dispersion is agitated, the first aqueous dispersion may also be centrifuged, and the supernatant recovered. Centrifugation separates mixed samples into homogenous component layers by spinning them at a high speed. In the present case, centrifugation causes an agitated aqueous dispersion to stratify into two different fractions. One fraction is a supernatant comprising the fraction of proteins that did not bind to the ion exchange material, and the other fraction is a concentrated solids fraction. When the ion exchange material is in the form of a free-flowing ion exchange resin, the concentrated solids fraction comprises the precipitate and the ion exchange resin. For example, when the ion exchange resin is an anion exchange resin, the proteins of the supernatant are positively charged and have a pI greater than the pH of the first aqueous dispersion; proteins with a pI less than the pH of the first aqueous dispersion will be negatively charged and will therefore be bound to the anion exchange resin. When the pH of the aqueous dispersion is approximately equal to the pI of albumin, the precipitated proteins will include albumin, as well as some proteins that have a pI equal or close to that of albumin (and which are thus zero charged). As previously discussed, at the theoretical pI of albumin (i.e., 5.9), some of the albumin molecules will be zero charged, while others will be slightly positively or negatively charged, depending on their pI. Even so, most of these slightly charged albumin molecules will still precipitate during centrifugation due to their high molecular weight and low charge density.

The length of time the aqueous dispersion should be centrifuged is dependent on the speed of the centrifugation. For example, if the aqueous dispersion is centrifuged at a low speed, it will typically be necessary to centrifuge the aqueous dispersion for a longer period of time in order to obtain a comparable degree of separation as would be obtained were the aqueous dispersion centrifuged at a greater speed for a shorter period of time. In general, as the centrifugation speed increases, the time required to obtain a desired degree of separation decreases. Preferably, the agitated aqueous dispersion is centrifuged at a force of at least about 500×g, more preferably at a force of at least about 1000×g, and still more preferably at a force of about 2000×g to about 8000×g; typically, the material will be centrifuged at a force of about 4000 to about 6000×g, and even more typically at a force of about 5000×g. In general, the material may be centrifuged for any length of time which does not degrade the protein; typically, centrifuge times will be in the range of about 10 to about 300 seconds. For example, in one embodiment, the agitated aqueous dispersion is centrifuged at a force of about 4000 to about 6000×g for about 30 seconds.

The supernatant may then be separated from the concentrated solids fraction by any suitable means known in the art. For example, in one embodiment, the supernatant is separated from the concentrated solids fraction by decanting the supernatant. In another embodiment, the supernatant is separated from the concentrated solids fraction by filtration.

This method thus allows proteins with a pI greater than that of albumin to be separated from a sample comprising albumin (e.g., when the pH of the combination is approximately equal to the pI of albumin). In addition, some proteins with the same pI range as albumin may be recovered using this method. Without wishing to be bound to any particular theory, it is believed that the recovery of these proteins (or protein fragments) may be due to the higher solubility of these proteins than albumin when their net charge is close to zero. As such, when the pH of the mixture is adjusted to a pH approximately equal to the theoretical pI of albumin, the albumin precipitates, while some proteins with a similar pI remain in the supernatant and are recovered along with the soluble proteins having a pI greater than that of albumin.

If no further separation is required, the resin may optionally be cleaned for future use by separating the resin from the precipitate and releasing bound proteins from the resin. This may be accomplished by forming a second aqueous dispersion comprising the separated first concentrated solids fraction, the second aqueous dispersion having a pH at which (i) all proteins are released from the anion exchange resin, and (ii) all precipitated albumin and proteins dissolve into the second aqueous dispersion. This may then be followed by the agitation, centrifugation, and separation steps, as previously described. The resulting supernatant will comprise the remaining proteins, including albumin, and the anion exchange resin will be free of bound proteins and ready for future use. In one embodiment, the pH of the second aqueous dispersion is about 1.0 or less, and preferably is about 1.0. The pH may be adjusted by a variety of agents known in the art, including acids such as 0.1 M HCl, or acidic buffers.

Albumin Separation

If desired, a further separation may be performed to separate albumin from other proteins present in the first concentrated solids fraction. In this embodiment, the method further comprises forming a second aqueous dispersion, the second aqueous dispersion comprising the separated first concentrated solids fraction as described above (e.g., comprising the anion exchange resin to which are bound proteins with a pI less than the pH of the first aqueous dispersion, and the precipitate). Preferably the pH of the second aqueous dispersion is a pH at which (i) albumin in the second aqueous dispersion dissolves into the second aqueous dispersion, and (ii) at least a fraction of protein bound to the anion exchange resin of the first concentrated solids fraction remains bound to the anion exchange resin. This step is followed by agitating the second aqueous dispersion, as described above; centrifuging the agitated second aqueous dispersion, as described above, to form a second supernatant fraction and a second concentrated solids fraction, the second concentrated solids fraction comprising the anion exchange resin; and separating the second supernatant from the second concentrated solids fraction.

The pH used in this step may vary depending on the desired separation. As previously discussed, preferably the pH of the second aqueous dispersion is a pH at which (i) albumin in the second aqueous dispersion dissolves into the second aqueous dispersion, and (ii) at least a fraction of protein bound to the anion exchange resin of the first concentrated solids fraction remains bound to the anion exchange resin. For example, the second aqueous dispersion will preferably have a pH less than the pH of the first aqueous dispersion. As the pH is decreased, precipitated albumin will resolubilize (i.e., will dissolve into the second aqueous dispersion) and may be subsequently removed. However, as the pH is decreased, more of the proteins bound to the anion exchange resin may also be released from the resin. If separation of albumin from the remaining proteins in the second aqueous dispersion is desirable, it is therefore preferable that the pH of the second aqueous dispersion be decreased only to the extent necessary for the albumin to dissolve into the dispersion, to minimize the release of bound proteins from resin. Therefore, the pH of the second aqueous dispersion advantageously has a pH of less than about 5.9, typically about 5.9 to about 4.9, and preferably has a pH of about 4.9. At this pH, albumin as well as the remaining proteins with a pI above 4.9 will be positively charged and will therefore be soluble and present in the supernatant, and the resulting second concentrated solids fraction will comprise the anion exchange resin, to which are bound negatively charged proteins having a pI less than the pH of the second aqueous dispersion. The resulting second concentrated solids fraction may optionally be further processed to separate proteins bound to the anion exchange resin based on their pI, as described below.

Precipitated albumin may also be dissolved into the second aqueous dispersion and subsequently recovered by decreasing the pH of the second aqueous dispersion in a stepwise manner to a pH wherein the albumin is dissolved into the second aqueous dispersion. Preferably, the pH is decreased in a stepwise manner to a pH of less than about 5.9, typically about 5.9 to about 4.9. As the pH is decreased, more of the precipitated albumin will be dissolved into the dispersion. Thus, in one embodiment, the albumin may be dissolved into the second aqueous dispersion by decreasing the pH of the second aqueous dispersion in a stepwise manner, wherein each pH adjustment is followed by agitating the adjusted mixture, centrifuging the agitated adjusted mixture to form a supernatant fraction and a concentrated solids fraction comprising the anion exchange resin, and separating the supernatant from the concentrated solids fraction, using the techniques as discussed above. Upon completion of this process, the resulting concentrated solids fraction comprises the anion exchange resin to which are bound proteins with a pI less than the pH of the resulting aqueous dispersion. The resulting concentrated solids fraction may then optionally be further processed to separate proteins bound to the anion exchange resin based on their pI, as described below.

If, after separation of the albumin, no further separation is required, the resin may optionally be cleaned for future use by releasing bound proteins from the resin, and separating the resin from any precipitate that may have formed. This may be accomplished by forming a third aqueous dispersion comprising the separated second concentrated solids fraction at a pH at which all proteins are released from the anion exchange resin. Advantageously, this pH may be about 1.0 or less, and preferably is about 1.0. This may then be followed by the agitation, centrifugation, and separation steps, as previously described. The resulting supernatant will thus comprise the remaining proteins, and the anion exchange resin will be free of bound proteins and ready for future use. Any of the acidic agents previously described may be used herein.

Separation and Fractionation of Proteins with a pI Less than Albumin

The second concentrated solids fraction comprising the anion exchange resin with bound proteins having a pI less than the pH of the second aqueous dispersion may be further processed to separate the proteins bound to the anion exchange resin from the anion exchange resin, or alternately, to separate the remaining proteins based on their pI. Thus, in another embodiment, the method further comprises forming a third aqueous dispersion comprising the separated second concentrated solids fraction at a pH at which (i) at least a fraction of protein bound to the anion exchange resin of the second concentrated solids fraction is released from the anion exchange resin, and (ii) the proteins are not denatured. This step may then be followed by agitating the third aqueous dispersion, as described above; centrifuging the agitated third aqueous dispersion to form a third supernatant fraction and a third concentrated solids fraction, the third concentrated solids fraction comprising the anion exchange resin; and separating the third supernatant from the third concentrated solids fraction.

Again, the pH used in this step may vary depending on the desired separation. For example, it may be desirable to separate the bound proteins from the anion exchange resin under non-denaturing conditions. Thus, as previously discussed, preferably the pH of the third aqueous dispersion is a pH at which (i) at least a fraction of protein bound to the anion exchange resin of the second concentrated solids fraction is released from the anion exchange resin, and (ii) the proteins are not denatured. For example, the third aqueous dispersion will preferably have a pH less than the pH of the second aqueous dispersion. As the pH is decreased, proteins bound to the anion exchange resin may be released from the resin, and may be subsequently collected. However, if the proteins are to be further analyzed or processed, it may be desirable to perform the separation under non-denaturing conditions so that the separated proteins retain their functionality. As will be appreciated by those skilled in the art, the pH at which proteins denature may vary depending on the protein. For example, many proteins (both intracellular and extracellular) denature at a pH value below 3.0. However, other proteins, such as certain lysosomal proteins and certain proteins found in the stomach of humans and other animals may retain activity even at pH values of about 1.0 to about 3.0. It is thus preferable that the pH chosen be one at which the protein of interest is not denatured. Therefore, in one embodiment, the pH of the third aqueous dispersion has a pH of less than the pH of the second aqueous dispersion but high enough so that the proteins of interest are not denatured. Advantageously, the third aqueous dispersion has a pH less than about 4.9, typically about 4.9 to about 3.0. In one embodiment, the pH of the third aqueous dispersion is about 3.3. In another embodiment, the pH of the third aqueous dispersion is about 3.0. The resulting third supernatant fraction may thus comprise positively charged proteins (i.e., proteins with a pI greater than the pH of the third aqueous dispersion), while proteins with a pI less than the pH of the third aqueous dispersion will be negatively charged and bound to the anion exchange resin.

The proteins bound to the anion exchange resin of the second concentrated solids fraction may also be separated and recovered based on their pI. In this embodiment, proteins may be released from the anion exchange resin by decreasing the pH of the third aqueous dispersion in a stepwise manner to a pH wherein protein is released from the anion exchange resin in one embodiment, the pH is decreased in a stepwise manner to a pH of less than about 4.9, typically about 4.9 to about 3.0. As the pH is decreased, more protein is released from the anion exchange resin. Each pH adjustment may then be followed by agitating the adjusted mixture, centrifuging the agitated adjusted mixture to form a supernatant fraction and a concentrated solids fraction comprising the anion exchange resin, and separating the supernatant from the concentrated solids fraction, using the techniques as discussed above. Upon completion of this process, the resulting concentrated solids fraction comprises the anion exchange resin to which are bound proteins with a pI less than the pH of the aqueous dispersion.

The number of fractions into which the bound proteins are separated will vary depending on the desired separation, as will the pH chosen for each pH adjustment. For example, in one embodiment, the pH may be decreased in a stepwise manner at a consistent interval. Alternately, the pH may be decreased in a stepwise manner at an inconsistent interval to produce protein fractions comprising proteins within varying pI ranges. As the pH is decreased, proteins are released from the anion exchange resin and recovered in the supernatant. In yet another embodiment, this method may be used to isolate proteins with a specific pH or within a specific pH range. In this embodiment, the pH of the aqueous dispersion is decreased to a pH so that only proteins with a pI above the target pI are released from the resin into the supernatant, followed by the agitation, centrifugation, and separation steps. The pH may then be decreased to a pH at which (i) proteins with a pI within the target pI range are released from the resin into the supernatant, and (ii) proteins with a pI less than the target pI range remain bound to the anion exchange resin, followed by the agitation, centrifugation, and separation steps, as previously described.

After the separation and fractionation of the proteins, the resin may optionally be cleaned for future use by releasing any remaining bound proteins from the resin, and separating the resin from the released proteins. This may be accomplished by forming a fourth aqueous dispersion comprising the separated third concentrated solids fraction at a pH at which all proteins are released from the anion exchange resin. Advantageously, this pH may be about 1.0 or less, and preferably is about 1.0. This may then be followed by the agitation, centrifugation, and separation steps as previously described. The resulting supernatant will thus comprise the remaining proteins, and the anion exchange resin will be free of bound proteins and ready for future use. Any of the acidic agents previously described may be used herein.

Separation Using a Cation Exchange Resin

In another embodiment, separation is performed using a cation exchange resin. A cation exchange resin may be used to perform a variety of separations, including: (i) separating a fraction of proteins with a pI less than that of albumin from a sample comprising albumin and other proteins; (ii) separating an albumin fraction from a sample comprising albumin and other proteins; (iii) separating a fraction of proteins with a pI greater than that of albumin from a sample comprising albumin and other proteins; and (iv) separating proteins with a pI greater than that of albumin into fractions based on their pI. Separation (i) is especially efficient when a cation exchange resin is used.

Separating Proteins with a pI Less than Albumin from a Sample

When using a cation exchange resin, the initial separation is preferably performed at a pH wherein albumin will precipitate. Therefore, in one embodiment, the present invention provides a method for separating albumin from a sample comprising albumin and other proteins using a cation exchange material. The method comprises combining the aqueous sample (comprising albumin and other proteins) with cation exchange material to form a first aqueous combination, the first aqueous combination comprising the sample and a cation exchange material. Preferably, the cation exchange material is in the form of a particulate resin and the aqueous combination is an aqueous dispersion of the particulate resin in the sample. Preferably, the cation exchange resin is capable of free-flowing movement relative to the rest of the dispersion, as discussed below, and is advantageously first equilibrated to the pH of the first aqueous dispersion prior to performing the separation. Alternately, instead of a free-flowing, particulate resin, the cation exchangers may be coated onto the interior surface or a portion of the interior surface of the container in which the separation is being performed, or may be present in other forms, such as described below. In this instance, the aqueous combination would comprise the sample (comprising albumin and other proteins) in contact with the cation exchangers, but would not necessarily be an aqueous dispersion.

This first aqueous dispersion is preferably formed at a pH at which albumin precipitates from the aqueous dispersion. As previously discussed, this pH is typically about 5.9, but may vary slightly depending on the degree of glycosylation of the albumin. Alternately, the first aqueous dispersion may be formed at a pH at which albumin does not precipitate or bind to the cation exchange resin, but proteins with a pI greater than the pH of the dispersion (including proteins with a pI greater than albumin) bind to the cation exchange material. In one embodiment, this pH is greater than about 5.9, typically about 5.9 to about 6.9, and preferably is about 6.9.

The aqueous dispersion may then be agitated and centrifuged as described above for separation using an anion exchange resin. When the pH of the aqueous combination is at or near the pI of albumin, agitation induces the albumin and proteins having a pI greater than the pH of the first aqueous dispersion to precipitate from the aqueous dispersion and/or to bind to the cation exchange resin. After the first aqueous dispersion is agitated, the agitated first aqueous dispersion may also be centrifuged to form a first supernatant fraction and a first concentrated solids fraction. When the ion exchange material is in the form of a free-flowing ion exchange resin, the concentrated solids fraction comprises the precipitate and the ion exchange resin. For example, when the ion exchange resin is a cation exchange resin, the proteins of the supernatant are negatively charged and have a pI less than the pH of the first aqueous dispersion; proteins with a pI greater than the pH of the first aqueous dispersion will be positively charged and will therefore be bound to the cation exchange resin. When the pH of the aqueous dispersion is approximately equal to the pI of albumin, the precipitated proteins will include albumin, as well as some proteins that have a pI equal or close to that of albumin (and which are thus zero charged). As previously discussed, at the theoretical pI of albumin (i.e., 5.9), some of the albumin molecules will be zero charged, while others will be slightly positively or negatively charged, depending on their pI. However, most of these slightly charged albumin molecules will still precipitate during centrifugation due to their high molecular weight and low charge density. The first supernatant may then be separated from the first concentrated solids fraction by any suitable means, such as described above for separation with an anion exchange resin.

This method thus allows proteins with a pI less than that of albumin to be separated from a sample comprising albumin and other proteins (e.g., when the pH of the combination is approximately equal to the pI of albumin). In addition, some proteins with the same pI range as albumin may be recovered using this method. Without wishing to be bound to any particular theory, it is believed that the recovery of these proteins (or protein fragments) may be due to the higher solubility of these proteins than albumin when their net charge is close to zero. As such, when the pH of the mixture is adjusted to a pH approximately equal to the theoretical pI of albumin, the albumin precipitates, while some proteins with a similar pI remain in the supernatant and are recovered along with the soluble proteins having a pI less than that of albumin.

If no further separation is required, the resin may optionally be cleaned for future use by separating the resin from the precipitate and releasing bound proteins from the resin. This may be accomplished by forming a second aqueous dispersion comprising the separated first concentrated solids, the second aqueous dispersion having a pH at which (i) all proteins are released from the cation exchange resin, and (ii) all precipitated albumin and proteins dissolve into the second aqueous dispersion. This may then be followed by the agitation, centrifugation, and separation steps, as previously described. The resulting supernatant will comprise the remaining proteins, including albumin, and the cation exchange resin will be free of bound proteins and ready for future use. In one embodiment, the pH of the second aqueous dispersion is about 14.0. The pH may be adjusted by a variety of agents known in the art, including bases such as 0.1 M NaOH and 0.1 M KOH, among others, and basic buffers.

Albumin Separation

If desired, a further separation may be performed to separate albumin from other proteins present in the first concentrated solids fraction. In this embodiment, the method further comprises forming a second aqueous dispersion, the second aqueous dispersion comprising the separated first concentrated solids fraction as described above (e.g., comprising the cation exchange resin to which are bound proteins with a pI greater than the pH of the first aqueous dispersion, and the precipitate). Preferably the pH of the second aqueous dispersion is a pH at which (i) albumin in the second aqueous dispersion dissolves into the second aqueous dispersion, and (ii) at least a fraction of protein bound to the cation exchange resin of the first concentrated solids fraction remains bound to the cation exchange resin. This step is followed by agitating the second aqueous dispersion, as described above; centrifuging the agitated second aqueous dispersion, as described above, to form a second supernatant fraction and a second concentrated solids fraction, the second concentrated solids fraction comprising the cation exchange resin; and separating the second supernatant from the second concentrated solids fraction.

The pH used in this step may vary depending on the desired separation. As previously discussed, preferably the pH of the second aqueous dispersion is a pH at which (i) albumin in the second aqueous dispersion dissolves into the second aqueous dispersion, and (ii) at least a fraction of protein bound to the cation exchange resin of the first concentrated solids fraction remains bound to the cation exchange resin. For example, the second aqueous dispersion will preferably have a pH greater than the pH of the first aqueous dispersion. As the pH is increased, precipitated albumin will resolubilize (i.e., will dissolve into the second aqueous dispersion) and may be subsequently removed. However, as the pH is increased, more of the proteins bound to the cation exchange resin may also be released from the resin. If separation of albumin from the remaining proteins in the second aqueous dispersion is desirable, it is therefore preferable that the pH of the second aqueous dispersion be increased only to the extent necessary for the albumin to dissolve into the dispersion, to minimize the release of bound proteins from the resin. Therefore, the pH of the second aqueous dispersion advantageously has a pH of greater than about 5.9, typically about 5.9 to about 6.9, and preferably has a pH of about 6.9. At this pH, albumin as well as the remaining proteins with a pI below 6.9 will be negatively charged and will therefore be soluble and present in the supernatant, and the resulting second concentrated solids fraction will comprise the cation exchange resin, to which will be bound positively charged proteins having a pI greater than the pH of the second aqueous dispersion. The resulting second concentrated solids fraction may optionally be further processed to separate proteins bound to the cation exchange resin based on their pI, as described below.

Precipitated albumin may also be dissolved into the second aqueous dispersion and subsequently recovered by raising the pH of the second aqueous dispersion in a stepwise manner to a pH wherein the albumin is dissolved into the aqueous dispersion. Preferably, the pH is increased in a stepwise manner to a pH of greater than about 5.9, typically about 5.9 to about 6.9. As the pH is increased, more of the precipitated albumin will be dissolved into the dispersion. Thus, in one embodiment, the albumin may be dissolved into the second aqueous dispersion by raising the pH of the second aqueous dispersion in a stepwise manner, wherein each pH adjustment is followed by agitating the adjusted mixture, centrifuging the agitated adjusted mixture to form a supernatant fraction and a concentrated solids fraction comprising the cation exchange resin, and separating the supernatant from the concentrated solids fraction, using the techniques as discussed above. Upon completion of this process, the resulting concentrated solids fraction comprises the cation exchange resin to which are bound proteins with a pI greater than the pH of the resulting aqueous dispersion. Optionally, the resulting concentrated solids fraction may be further processed to separate bound proteins based on their pI, as discussed below.

If, after separation of the albumin, no further separation is required, the resin may optionally be cleaned for future use by releasing bound proteins from the resin, and separating the resin from any precipitate that may have formed. This may be accomplished by forming a third aqueous dispersion comprising the separated second concentrated solids fraction at a pH at which all proteins are released from the cation exchange resin. Advantageously, this pH may be about 14.0. This may then be followed by the agitation, centrifugation, and separation steps, as previously described. The resulting supernatant will thus comprise the remaining proteins, and the cation exchange resin will be free of bound proteins and ready for future use. Any of the basic agents previously described may be used herein.

Separation and Fractionation of Proteins with a pI Greater than Albumin

The second concentrated solids fraction comprising the cation exchange resin with bound proteins having a pI greater than the pH of the second aqueous dispersion may be further processed to separate the proteins bound to the cation exchange resin from the cation exchange resin, or alternately, to separate the remaining proteins based on their pI. Thus, in another embodiment, the method further comprises forming a third aqueous dispersion comprising the separated second concentrated solids fraction at a pH at which (i) at least a fraction of protein bound to the cation exchange resin of the second concentrated solids fraction is released from the cation exchange resin, and (ii) the proteins are not denatured. This step is followed by agitating the third aqueous dispersion, as described above; centrifuging the agitated third aqueous dispersion to form a third supernatant fraction and a third concentrated solids fraction, the third concentrated solids fraction comprising the cation exchange resin; and separating the third supernatant from the third concentrated solids fraction.

Again, the pH used in this step may vary depending on the desired separation. For example, it may be desirable to separate the bound proteins from the cation exchange resin under non-denaturing conditions. Thus, as previously discussed, preferably the pH of the third aqueous dispersion is a pH at which (i) at least a fraction of protein bound to the cation exchange resin of the second concentrated solids fraction is released from the cation exchange resin, and (ii) the proteins are not denatured. For example, the third aqueous dispersion will preferably have a pH greater than the pH of the of the second aqueous dispersion. As the pH is increased, proteins bound to the cation exchange resin may be released from the resin, and may be subsequently collected. However, if the proteins are to be further analyzed or processed, it may be desirable to perform the separation under non-denaturing conditions so that the separated proteins retain their functionality. As will be appreciated by those skilled in the art, the pH at which proteins denature may vary depending on the protein. For example, most proteins will be denatured at a pH value above 11.0, however, other proteins may retain activity even at pH values of 11.0 and above. Therefore, in one embodiment, the pH of the third aqueous dispersion has a pH of greater than the pH of the second aqueous dispersion but low enough so that the proteins of interest are not denatured. Advantageously, the third aqueous dispersion has a pH greater than about 6.9, typically about 6.9 to about 11.0. In one embodiment, the pH of the third aqueous dispersion is about 8.0. In another embodiment, the pH of the third aqueous dispersion is about 11.0. The resulting third supernatant fraction may thus comprise negatively charged proteins (i.e., proteins with a pI less than the pH of the third aqueous dispersion), while proteins with a pI greater than the pH of the third aqueous dispersion will be positively charged and bound to the cation exchange resin.

The proteins bound to the cation exchange resin of the second concentrated solids fraction may also be separated and recovered based on their pI. In this embodiment, proteins may be released from the cation exchange resin by raising the pH of the third aqueous dispersion in a stepwise manner to a pH wherein protein is released from the cation exchange resin. In one embodiment, the pH is increased in a stepwise manner to a pH of greater than about 6.9, typically about 6.9 to about 11.0. As the pH is increased, more protein is released from the cation exchange resin. Each pH adjustment may then be followed by agitating the adjusted mixture, centrifuging the agitated adjusted mixture to form a supernatant fraction and a concentrated solids fraction comprising the cation exchange resin, and separating the supernatant from the concentrated solids fraction, using the techniques as discussed above. Upon completion of this process, the resulting concentrated solids fraction comprises the cation exchange resin to which are bound proteins with a pI greater than the pH of the aqueous dispersion.

The number of fractions into which the bound proteins are separated will vary depending on the desired separation, as will the pH chosen for each pH adjustment. For example, in one embodiment, the pH may be increased in a stepwise manner at a consistent interval. Alternately, the pH may be increased in a stepwise manner at an inconsistent interval to produce protein fractions comprising proteins with varying pI ranges. As the pH is increased, proteins are released from the cation exchange resin and recovered in the supernatant. In yet another embodiment, this method may be used to isolate proteins with a specific pH or within a specific pH range. In this embodiment, the pH of the aqueous dispersion is increased to a pH at which only proteins with a pI below the target pI are released from the resin into the supernatant, followed by the agitation, centrifugation, and separation steps. The pH may then be increased to a pH at which (i) proteins with a pI within the target pI range are released from the resin into the supernatant, and (ii) proteins with a pI greater than the target pI range remain bound to the cation exchange resin, followed by the agitation, centrifugation, and separation steps, as previously described.

After the separation and fractionation of the proteins, the resin may optionally be cleaned for future use by releasing any remaining bound proteins from the resin, and separating the resin from the released proteins. This may be accomplished by forming a fourth aqueous dispersion comprising the separated third concentrated solids fraction at a pH at which all proteins are released from the cation exchange resin. Advantageously, this pH may be about 14.0. This may then be followed by the agitation, centrifugation, and separation steps as previously described. The resulting supernatant will thus comprise the remaining proteins, and the cation exchange resin will be free of bound proteins and ready for future use. Any of the basic agents previously described may be used herein.

Buffers

Any agent or buffer capable of adjusting the protein sample or aqueous dispersion to the desired pH may be used in the methods described herein. A buffer is a solution that is resistant to changes in pH, such as those changes that result from the addition of an acid or a base to the buffer solution. A buffer generally comprises at least one buffering component, i.e., a weak base, a weak acid, or combinations thereof. A weak acid or a weak base can be described by a dissociation constant ($K_d$), which is a measure of the extent to which a dissociation reaction, AB↔A+B, proceeds at equilibrium. In the case of a strong acid or a strong base, the above reaction would typically be written with a regular forward arrow, because the equilibrium lies very far to the right, i.e. favoring the products (the dissociated ions). It is for this reason that a strong acid alone or a strong base alone cannot function as a buffer. A dissociation constant is expressed by the following equation, where [A], [B], and [AB] indicate the concentrations of A, B, and AB, respectively:

$$K_d = [A^-][B]/[AB].$$

A strong acid or a strong base generally cannot be described by a dissociation constant, because the equilibrium lies so far to the right, as described above, and the products of the reaction are so favored (the denominator in the above reaction would approach zero). For a weak acid, this dissociation constant is generally referred to as the acid dissociation constant ($K_a$) and is a measure of how likely an acid is to release a proton in the dissociation reaction HA⇌H$^+$+A$^-$, proceeding at equilibrium. An acid dissociation constant is expressed by the following equation:

$$K_a = [H^+][A^-]/[HA].$$

The $pK_a$ of a weak acid (or a protonated base) is expressed by the following equation:

$$pK_a = -\log(K_a).$$

The $pK_a$(s) of a buffer's component(s) is closely related to the buffer's buffer range. Generally, a buffer can be described by both its buffer capacity, including acid buffer capacity and base buffer capacity, and its buffer range. Acid buffer capacity is defined as the number of moles of strong acid per liter of buffer that is required to lower the pH of the buffer by 1 unit. Base buffer capacity is defined as the number of moles of strong base per liter of buffer that is required to raise the pH of the buffer by 1 unit. Buffer range is the pH range over which a buffer neutralizes added acids or bases and maintains a fairly constant pH (+/−1 pH unit). A buffer's buffer range typically spans one pH unit above or below the $pK_a$ of a buffer component. For example, alloxanic acid has a $pK_a$ of about 6.64 and a buffer range of about pH 5.64 to about pH 7.64. One skilled in the art would thus select a buffer comprising a component with a $pK_a$ that is close to a desired pH. For buffers comprising more than one component, the buffer range would be computed in the same way with respect to each individual component. For example, a buffer comprising acetic acid ($pK_a$ of about 4.7) and ethanolamine ($pK_a$ of about 9.6) would have a split buffer range of about pH 3.7 to about pH 5.7 and about pH 8.6 to about pH 10.6. The gaps in such a split buffer range, i.e., about pH 5.7 to about pH 8.6, indicate pH ranges where the buffer has substantially no buffer capacity.

If, when the $pK_a$s of buffer components are ordered from lowest to highest, there is not a difference of approximately 2 or more units between any two consecutive $pK_a$s, then the buffer range will span from one pH unit below the lowest $pK_a$ to one pH unit above the highest $pK_a$, without any gaps where changes in pH are not resisted. Certain buffer components are polyprotic, meaning they contain more than one proton (hydrogen) per molecule. Polyprotic buffer components release protons in a step wise manner, releasing a proton at each step, and the total number of steps depends on the total number of protons per molecule. For each step, there is a different dissociation constant, i.e. $pK_{a1}$, $pK_{a2}$, $pK_{a3}$, etc. A buffer comprising a polyprotic weak acid is thus described by more than one pKa value. When calculating the buffer range of a buffer comprising a polyprotic acid, the procedure described above is followed and all of the $pK_a$s are ordered from lowest to highest. Again, if there is not a difference of approximately 2 or more units between any two consecutive $pK_a$s, then the buffer range will span from one pH unit below the lowest $pK_a$ to one pH unit above the highest $pK_a$. If there is a difference of approximately 2 or more units between any two consecutive $pK_a$s, then the buffer will have a split buffer range, as described above. For example, a buffer comprising bis-tris propane ($pk_{a1}$ of about 9; $pK_{a2}$ of about 6.8) and piperazine ($pK_{a1}$ of about 9.8; $pK_{a2}$ of about 5.6) would have a buffer range of about pH 4.6 to about pH 10.8.

In addition to having the ability to resist pH changes within a buffer range that typically spans one pH unit above or below the $pK_a$ of a buffer component, buffers themselves are also characterized by a pH. This pH varies with the concentrations of weak acid and conjugate base or weak base and conjugate acid. The pH of a buffer is generally described by the Henderson-Hasselbalch equation:

$$pH = pK_a + \log([A^-]/[HA]).$$

Derivatives of this basic equation exist which allow one to calculate the pH of a buffer comprising multiple components. Thus, buffers are not only capable of resisting pH changes within a certain pH range (buffer range), they are also capable of adjusting a particular solution, including a biological sample or an aqueous dispersion, to a desired pH. By further using a buffer to modify the pH of a solution, as opposed to using a strong acid alone or a strong base alone, one is able to make very slight modifications to the pH, changing the pH in a very controlled fashion. This is true because the buffer that is added to the buffered solution changes the concentrations of both the weak acid and its conjugate base or both the weak base and its conjugate acid. In contrast, if, for example, a strong base, such as sodium hydroxide (NaOH), is added to adjust (raise) the pH of a buffered solution comprising a weak acid, the added hydroxide ions (OH⁻) consume the protons (H⁺) in solution, causing the weak acid (HA) to dissociate in order to replenish the supply of H⁺ and maintain $K_a$. Eventually, the concentration of HA is depleted to such an extent that the loss of H⁺ can no longer be counteracted and the pH begins to increase more rapidly, i.e. the solution loses its capacity to buffer. As described above, if a buffer is used to raise the pH of such a buffered solution instead of a strong base, the buffer would replenish the supply of HA to some extent, thereby avoiding a rapid increase in pH.

Because of all the above-described characteristics of a buffer, a buffer is a preferred agent for adjusting an aqueous dispersion to a desired pH. Preferably a buffer is selected wherein the target pH (or pHs) of the aqueous dispersion falls within the buffer's buffer range. For example, if the desired pH of a sample is 3.3, a buffer with a buffer range that included 3.3 would preferably be selected. Preferably, the pH of 3.3 is not at the lower or higher end of this range, so that the pH can be modified in further separation steps without the loss of buffer capacity. For example, a buffer component with a $pK_a$ of 3.3 may be selected, in order to give a buffer range of about pH 2.3 to about pH 4.3. It is generally more preferable to select a buffer characterized by a broader buffer range, such as about pH 2 to about pH 9.

Using the principles described herein, one skilled in the art may readily choose a buffer appropriate for the desired separation. The buffer may comprise one or more buffer components. If the buffer comprises multiple buffer components (or a single component with multiple $pK_a$s), it is generally preferable that the buffer does not have a split buffer range, as described above.

In general, any agent with a $pK_a$ may be used as a buffer component. Examples of suitable buffer components that may be used alone, or combined with other buffer components to form a buffer include, but are not limited to bis-tris propane ($pK_{a1}$ about 9.0; $pK_{a2}$ about 6.8), piperazine ($pK_{a1}$ about 9.8; $pK_{a2}$ about 5.6); alloxanic acid ($pK_a$ about 6.64); 1,2-propanediamine ($pK_{a1}$ about 9.8; $pK_{a2}$ about 6.6); histamine ($pK_{a1}$ about 9.8; $pK_{a2}$ about 6); benzimidazole ($pK_a$ about 5.5); isoquinoline ($pK_a$ about 5.4); 7-isoquinolinol ($pK_{a1}$ about 8.9; $pK_{a2}$ about 5.7); 2-methylquinoline ($pK_a$ about 5.8); 4-methylquinoline ($pK_a$ about 5.7); acridine ($pK_a$ about 5.6); ethanolamine ($pK_a$ about 9.6); trimethylamine ($pK_a$ about 9.8); N,N-dimethylglycine ($pK_a$ about 9.9); noradrenaline ($pK_{a1}$ about 9.7; $pK_{a2}$ about 8.6); pyridine ($pK_a$ about 5.2), acetic acid ($pK_a$ about 4.7), lactic acid (pKa about 3.8), chloroacetic acid (pKa about 2.8), glycocyamine (pKa about 2.8); chloroaniline (pKa about 2.8); dinicotinic acid ($pK_a$ about 2.8); 4-aminoazobenzene ($pK_a$ about 2.82); formic acid ($pK_a$ about 3.75); 3-chloropropanoic acid ($pK_a$ about 3.98); acetoacetic acid ($pK_a$ about 3.6); N-acetylglycine ($pK_a$ about 3.7); uric acid ($pK_a$ about 3.9); 6-chloropteridine ($pK_a$ about 3.7); thiazolamine ($pK_a$ about 5.3); melamine ($pK_a$ about 5); benzimidazole ($pK_a$ about 5.4); N,N-dimethylaniline ($pK_a$ about 5.2); N-ethylaniline ($pK_a$ about 5.1); 5-methylquinoline ($pK_a$ about 5.2); itaconic acid ($pK_{a1}$ about 5.45; $pK_{a2}$ about 3.85); m-phtalic acid ($pK_{a1}$ about 4.6; $pK_{a2}$ about 3.6); malonic acid ($pK_{a1}$ about 5.7; $pK_{a2}$ about 2.8); adipic acid ($pK_{a1}$ about 5.4; $pK_{a2}$ about 4.4); and heptanedioic acid ($pK_{a1}$ about 5.6; $pK_{a2}$ about 4.7), among others. Other examples of suitable buffer components are known in the art and are described in, for example, Kang, X Z, and Frey, D. D., "Chromatofocusing using micropellicular column packings with computer-aided design of the elution buffer composition", Analytical Chemistry, (2002) Vol. 74(5), pp.1038-1045.

In addition to using a single buffer, a buffer system comprising two or more buffers may also be used. In one embodiment, the buffer used herein is a buffering system comprising a combination of a first buffer and a second buffer. Preferably, the first buffer is slightly basic, with a pH in the range of about 7.0 to about 9.0, and more preferably about 8.0, and with a buffer range of about pH 4.6 to about pH 10.8. The second buffer is preferably acidic, with a pH in the range of about 2.3 to about 4.3, more preferably about 3.3, and with a buffer range of about pH 1.8 to about pH 6.2. Buffering systems comprising more than two component buffers may also be employed.

One example of a suitable buffer system comprises a first buffer comprising bis-tris propane and piperazine, and a second buffer comprising pyridine, acetic acid, lactic acid, and chloroacetic acid. As will be apparent to one skilled in the art, the pH of such a buffer system may be varied by altering the ratios of the first and second buffers in the buffer system. One example of altering the percentage of component buffers in a buffer system to change the pH of the buffer system is shown in Table 2. In Table 2, buffer A comprises bis-tris propane and piperazine, and buffer B comprises pyridine, acetic acid, lactic acid, and chloroacetic acid.

One skilled in the art can readily design other appropriate buffer systems, using the information provided herein.

Ion Exchange Materials

Charged molecules such as proteins, peptides, and/or amino acids, as well as other solutes, may be separated from the samples by means of ion exchange. Ion exchange materials, such as ion exchange resins, typically comprise two types of ions: ions bound within or on the resin, and an oppositely charged counterion. When the resin is contacted with a sample, charged molecules in the sample may displace the counterions and bind to the resin. During the separation process, the charged molecules bound to the resin may be competitively and sequentially displaced or eluted from the resin in an order that is inversely related to the binding affinity of the charged molecules by raising the concentration of counterions in the sample. For more a more detailed discussion of ion exchange, see Moore, et al., "Chromatography of amino acids on sulfonated polystyrene resins," 1958, *Analytical Chemistry*, 30:1185-1190.

In general, there are four major types of ion exchange resins or media. Strong cation exchange resins/media are strongly acidic, and generally contain fully ionized acidic groups such as sulfonic acid groups or the corresponding salts. These exchangers are negatively charged, and bind cations very strongly. In contrast, strong anion exchange resins/media are strongly basic, and generally contain highly ionized basic groups such as quaternary ammonium groups. Strong anion exchange resins are typically classified into two types: Type I resins contain trialkyl ammonium chloride or hydroxide (e.g., Dowex-1 (trimethylbenzyl ammonium), etc.); and Type II resins contain dialkyl 2-hydroxyethyl ammonium chloride or hydrochloride (e.g., Dowex-2 (dimethyl-2-hydroxyethylbenzyl ammonium), etc.). These exchangers are positively charged, and bind anions very strongly. The exchange capacity of strong acid or base resins is typically independent of the pH of the sample contacting the resin.

Weak cation exchange resins/media contain weak acids, such as carboxylic acid groups or the corresponding salts (e.g., carboxymethyl (CM) cellulose, Chelex-100, etc.). Since the degree of dissociation of a weak acid resin is influenced by pH, resin capacity depends in part on solution pH. For example, a typical weak acid resin has very limited capacity below a pH of 6.0. Thus, by "weak cation exchange resin" or "weak cation exchange material" it is meant that the exchanger is a weak acid that will be negatively charged when the pH is above the $pK_a$ of the exchanger. In contrast, weak anion exchange resins/media contain weak bases, such as ammonium chloride or hydroxide (e.g., diethylaminoethyl (DEAE) and Dowex (poylamine)). Since the degree of ionization of a weak base resin is influenced by pH, resin capacity depends in part on solution pH. For example, weak base resins typically exhibit minimum exchange capacity above a pH of 7.0. Thus, by "weak anion exchange resin" or "weak anion exchange material" it is meant that the exchanger is a weak base that will be positively charged when the pH is below the $pK_a$ of the exchanger.

Ion exchange resins may comprise a variety of charged groups. For example, the anion exchange resin may comprise charged groups such as diethylaminoethyl (DEAE), quaternary aminoethyl (QAE), quaternary ammonium (Q), and/or other primary, secondary, tertiary ($pK_a \approx 9.8$), or quaternary amines. The cation exchange resin may comprise charged groups such as carboxymethyl (CM), sulfopropyl (SP), and/or methyl sulfonate (S). These charged groups may be attached to a variety of core materials including those that are agarose-based (e.g., SEPHAROSE CL-6B, SEPHAROSE FAST FLOW, and SEPHAROSE HIGH PERFORMANCE), cellulose-based (e.g., DEAE SEPHACEL), dextran-based (e.g., SEPHADEX), silica-based, and synthetic polymer based.

Although any of a variety of ion exchangers may be used in accordance with the methods described herein to bind soluble, charged proteins, peptides, amino acids, and/or other charged molecules, preferably the ion exchangers are weak anion exchangers or weak cation exchangers. In one embodiment, the anion exchange resin used herein comprises polybuffer exchanger 94 (PBE 94) resin (G.E. Healthcare). PBE 94 is a weak anion exchange resin comprising mixed quaternary and tertiary amines. In another embodiment, the cation exchange resin used herein preferably comprises carboxymethyl ($pK_a \approx 4.5$) with a sepharose core material.

Because the aqueous dispersions described herein (e.g., comprising a sample comprising albumin and other proteins, ion exchange resin, and optionally a buffer or other pH adjusting agent) may be agitated to better facilitate separation of albumin and proteins, in one embodiment, the resin used herein is capable of free-flowing movement relative to the rest of the dispersion. For example, in this embodiment, the resin particles are preferably capable of independent movement relative both to other resin particles and relative to the other dispersion components. The aqueous dispersions comprising the free-flowing resin may therefore be amenable to agitation, in contrast to the relatively immobile state of resin that is packed in a column.

Although discussed herein primarily in terms of free-flowing resin, it is to be understood that the ion exchange material used in the methods described herein may be in various formats. For example, the ion exchangers may be coated on beads, may be in the form of a membrane ion exchange resin, may be coated onto the interior surface or a portion of the interior surface of the container in which the separation is being performed, and/or may be coated on an object, such as a magnetic stir bar or rod, present in the container in which the separation is being performed. Other suitable formats for the ion exchangers will be apparent to those skilled in the art.

As various changes could be made in the above methods without departing from the scope of the invention, it is intended that all matter contained in the above description and in the examples given below, shall be interpreted as illustrative and not in a limiting sense.

EXAMPLES

The present invention is illustrated by the following examples which are merely for the purpose of illustration and are not to be regarded as limiting the scope of the invention or manner in which it may be practiced.

Example 1

Fractionation of Plasma Protein Sample

In this example albumin was fractionated by column chromatography and prefractionation using PBE 94. The efficiency of these methods was measured by one-dimensional electrophoresis, two-dimensional electrophoresis, and western blot.

1.1 Chromatofocusing of Human Plasma Protein Samples

In this example, chromatofocusing was performed on a plasma protein sample containing 15 human plasma proteins. The plasma proteins contained in the sample are listed in Table 1. 66% of the sample total mass constituted albumin.

The system used for this analysis is an Äkta purifier (Amersham Pharmacia Corporation, Uppsala, Sweden). Chromatofocusing is an ion-exchange chromatography technique in which the proteins are bound to an anion exchanger, Polybuffer Exchanger 94 (PBE 94), then eluted by a continuous decrease of the buffer pH so that proteins elute in order of their isoelectric points. PBE 94 is a weak anion exchange resin. The matrix is polystyrene/divinyl benzene. The ion exchanger type is mixed quaternary and tertiary amines. The working range of this resin is pH 4 to 9. PBE 94 was packed in a 250 mm×5 mm column according to the manufacturer's instructions.

The column was first equilibrated with buffer A (12.5 mM bis-tris propane and 12.5 mM piperazine, pH 7.8) at a flow rate of 1 mumin until the solution eluted had a stable pH of 7.8. A volume of 22.5 μL of the plasma protein sample containing 1.355 mg of proteins was dissolved in 500 μL of buffer A, injected in the column, and the concentration of buffer B (12.5 mM pyridine, 12.5 mM acetic acid, 12.5 mM lactic acid and 12.5 mM chloroacetic acid, pH 3.3) is set from 0 to 100% in 60 minutes, held on 100% for 30 minutes, then a 0.1 M HCl solution was pumped to elute the acidic proteins. The column was quickly reequilibrated with buffer A to avoid any damage secondary to the low pH. Fractions were collected every 2 minutes. A UV detector at 215 nm and a pH meter were used respectively for the detection of eluting proteins and to monitor the pH change of the eluting solution.

The chromatogram of separation of the human plasma proteins based upon pI generated several peaks (FIG. 1). The peak with the largest area (FIG. 1) is thought to represent albumin, as albumin constitutes 66% of this sample, and this peak is formed at a pH of eluant close to the pI of albumin (pI 5.92).

TABLE 1

Composition of 15 Human Plasma Protein Sample

| Protein | Mass (μg) |
| --- | --- |
| transthyretin | 0.099 |
| albumin | 179.6 |
| α1-glycoprotein | 3 |
| antitrypsin | 5.45 |
| ceruloplasmin | 1 |
| macroglobulin | 7.4 |
| haptoglobulin | 4 |
| transferrin | 11 |
| complement C3C | 5 |
| complement C4 | 0.7 |
| C-reactive protein | 0.2 |
| IgG | 44 |
| IgA | 8.8 |
| IgM | 3.6 |
| α1-antichymotrypsin | 1.1 |

1.2 Nonporous Silica-Reversed-Phase-High Performance Liquid Chromatography-Electrospray Ionization-Time of Flight-Mass spectrometry (NPS-RP-HPLC-ESI-TOF-MS)

To test the efficiency of the separation of the sample that occurred in Example 5, liquid chromatography electrospray ionization mass spectrometry was carried out for the fractions labeled 1 to 4 in FIG. 1.

A nonporous silica column allows for the rapid separation of a large number of proteins with high recovery compared to porous columns. A System Gold 125 S solvent module (Beckman Coulter Inc., Fullerton, Calif., USA) pump and a 4.6 mm×33 mm nonporous column (Eprogen Inc., Darien, Ill., USA) were used for the RP-H PLC separation. 10 μL of the 2 mL fractions (fractions 1 and 2) were injected, solvent A was water-0.1% trifluoroacetic acid (TFA) and solvent B was acetonitrile-0.1% TFA. The gradient was run from 0 to 40% B in 5 minutes, 40% to 70% in 20 minutes, 70% to 100% in 2 minutes, and was held on 100% for 5 minutes at a flow rate of 200 μL/min. The temperature of the column was held constant at 60° C. to improve the resolution and reduce the pressure. The detector used was a Beckman gold UV detector; proteins were detected at 215 nm. The outlet of the detector was connected to the inlet of a T100LC (Jeol, Dearborn, Mass., USA), electrospray ionization time of flight mass spectrometer. The mass spectrometer parameters were: Source capillary 3000 V, sample cone 20 V, RF lens 100 V, Extraction cone 5 V, Desolvation temperature 250° C., and source temperature 80° C. Deconvolution was carried out using the Jeol ESI Deconvolution V2 program.

Figure 2B:
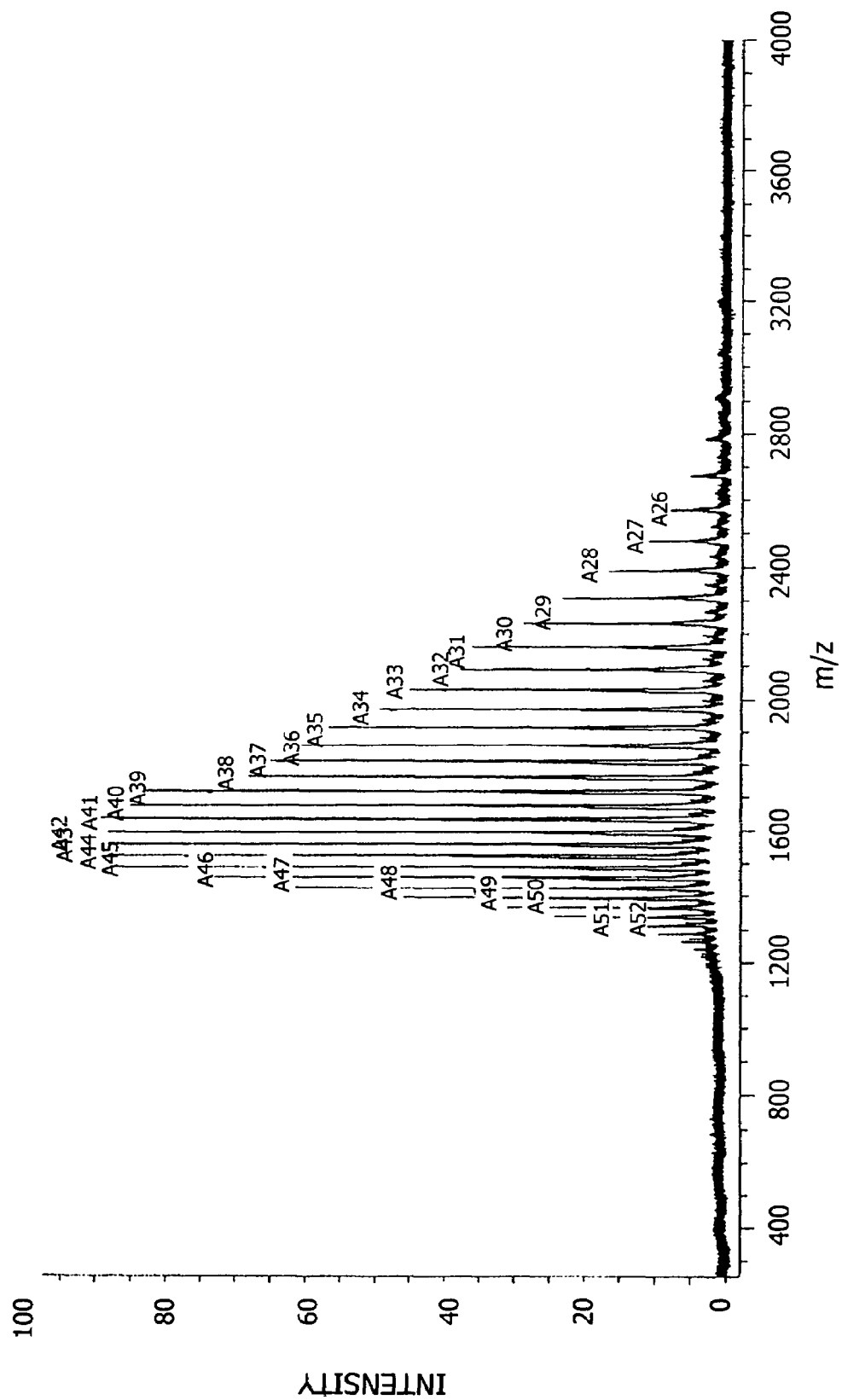
FIG. 2B is the ESI-TOF-MS measured spectrum for the peak shown at 12.5 minutes in the chromatogram of FIG. 2A. The number at the top of each peak represents the ionization state of the 66,804.84 Da albumin.

This separation yielded two peaks (FIG. 2A): a peak at 1 min. representing the salts and ions from the buffers used for the chromatofocusing, and a peak at 12.5 min. The deconvolution of the measured spectrum (FIG. 2B) of this peak showed a molecular mass ranging from 65 to 70 kDa (FIG. 2C), corresponding to the molecular masses of the different glycation states of albumin. This was taken as proof that the peak in question represents albumin. Other low-intensity peaks were present as well. For the liquid chromatography electrospray ionization mass spectrometry of the other fractions, deconvolution was made impossible by the presence of several peaks (data not shown).

1.3 Sodium Dodecyl Sulfate-Polyacrylamide Gel Electrophoresis (SDS-Page) of the Fractions Collected from the Chromatofocusing Separation The 2 mL fractions (fractions 1 to 4) from the chromatofocusing separation of Example 5 were vacuum dried and reconstituted with 150 μL of 50 mM Tris-HCl (pH 6.8), 2% SDS, 0.1% bromophenol blue, and 10% glycerol. 30 μL of this mixture was then applied on a 12% polyacrylamide SDS gel. Gels were electrophoresed at 30 V for 30 minutes, then at 50 mA per gel for 45 minutes.

SDS-PAGE analysis of this fraction reveals several proteins other than albumin (FIG. 3). Therefore, albumin cannot be separated from the other plasma proteins using chromatofocusing.

The results (see FIG. 3) show that each fraction contained several proteins other than albumin, with similar pI values. It can be concluded that albumin cannot be isolated from the other proteins using chromatofocusing, and that the elution of albumin from the column occurred between the 75% and 90% concentrations of buffer B (see FIG. 1). The idea of isolating albumin between these two concentrations emerged, and instead of packing PBE 94 resin in a column, 1 mL of this resin was pipefted into an eppendorf tube, where the isoelectric elimination of albumin was accomplished according to the procedure of Example 1.5.

1.4 pH Calibration for the Batch Chromatography

In this example, albumin was gradually resolubilized by decreasing the pH of the buffer used in a stepwise manner. The percent of buffer A (12.5 mM bis-tris propane and 12.5 mM piperazine; pH 8) and buffer B (12.5 mM pyridine, 12.5 mM acetic acid, 12.5 mM lactic acid, and 12.5 mM chloroacetic acid; pH 3.3) useful for isolating albumin was determined.

1 mL of the PBE 94 resin was pipetted into a 1.5 mL centrifuge tube. The resin was then washed twice with buffer A. The tube was vortexed for 30 seconds, centrifuged at 5000×g for 1 minute, and the supernatant was aspirated after each wash. 4.5 μL of 15 human plasma protein sample (as described in Example 1 and Table 1) containing 275 μg of plasma proteins was diluted with buffer A to a volume of 350 μL and added to the resin. The resin was vortexed for 30 seconds, centrifuged at 5000×g for 1 minute, and the supernatant was pipetted out. Then, 350 μL of a series of different buffer compositions with increasing percentages of buffer B were sequentially added to gradually decrease the pH of the solution as described in Table 2. Following each buffer addition, the tube was vortexed for 30 seconds, centrifuged at 5000×g for 1 minute, and the supernatant was removed. Fifteen fractions were collected, vacuum dried, reconstituted with 30 μL of 50 mM ros-HCl (pH 6.8), 2% SDS, 0.1% bromophenol blue and 10% glycerol, and applied to a 10% polyacrylamide SDS gel. Supernatant collected after addition of each buffer composition was added to the gel twice (see FIGS. 4A-4D). Gels were electrophoresed at 30 V for 30 minutes, then at 50 mA per gel for 45 minutes.

Figure 4A:
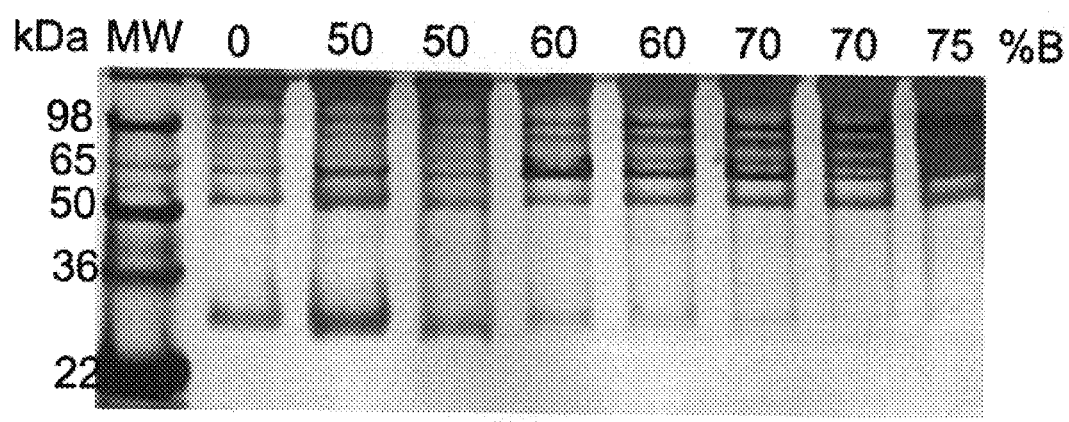
FIGS. 4A and 4B depict a 1-dimensional gel electrophoresis of the supernatant recovered after the addition of buffers consisting of buffer A and buffer B to a plasma protein sample comprising 275 µg of proteins, as described in Example 1. The percent of buffer B (v/v) is marked on the horizontal axis. The molecular weight (kDa) standards are marked on the vertical axis.
Figure 4B:
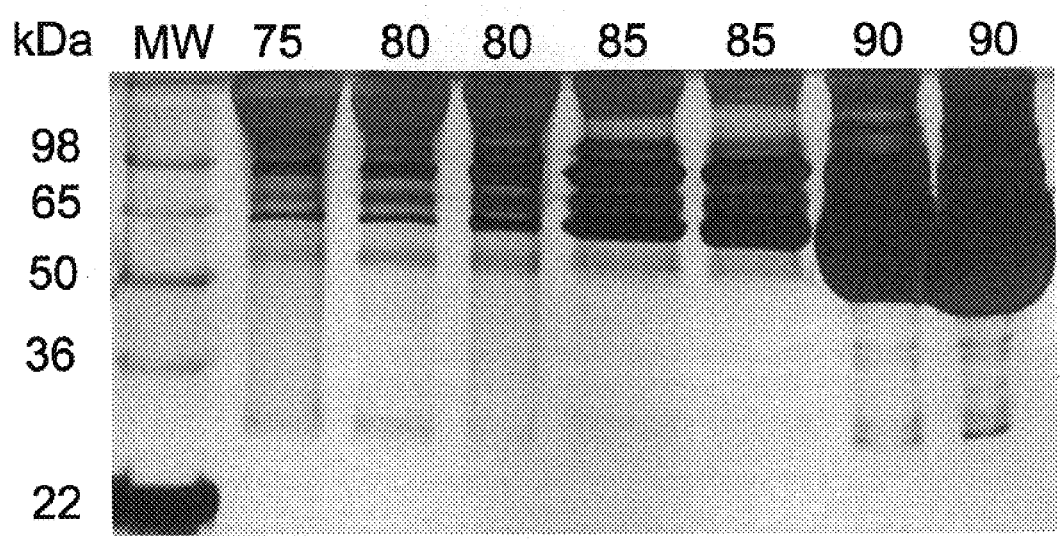
Figure 4C:
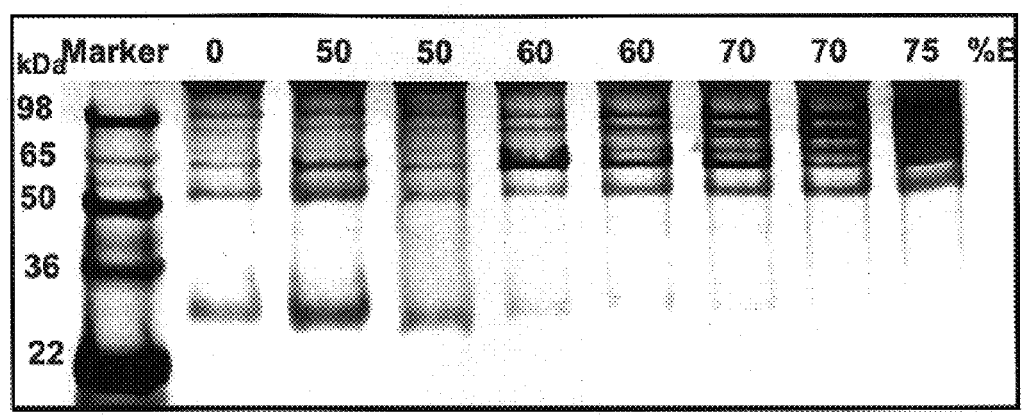
FIG. 4C and FIG. 4D depict the same gels as FIGS. 4A and 4B however.
Figure 4D:
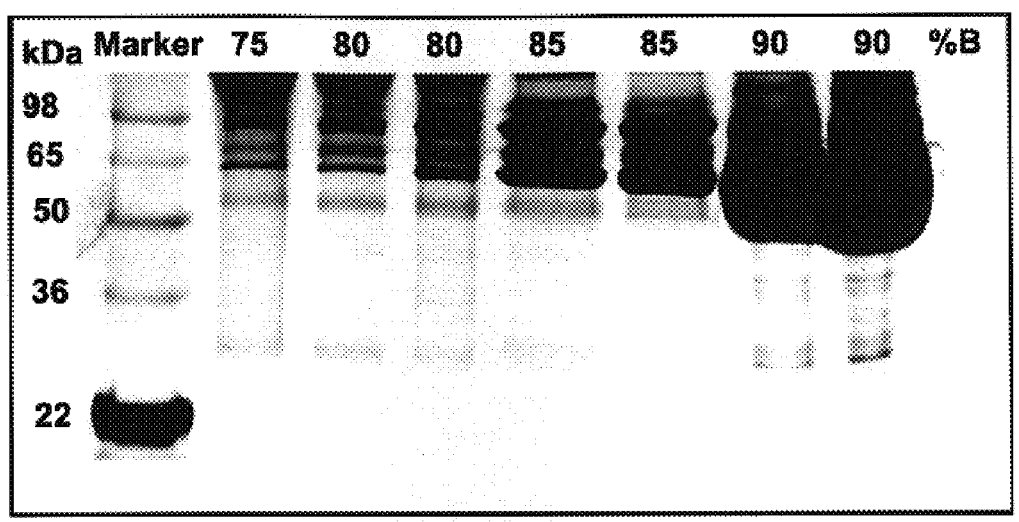

The gels show that for pHs above 5.4, corresponding to a percentage of buffer B lower than 75%, no major 65 kDa bands were shown on a silver-stained gel (FIGS. 4A and 4C). An increasing 65 kDa band appears when the pH is adjusted to values lower than 5, corresponding to a percentage of buffer B higher than 80% (FIGS. 4B and 4D), and this band becomes the dominant feature when the pH is adjusted to a value of 4.7 (90% B). The resolubilization of albumin in the aqueous phase occurred between the 75 and 90% concentrations of buffer B.

TABLE 2

The different compositions of Buffer A and Buffer B added to the resin and the resulting gradually decreasing pH.

| % buffer A | % buffer B | pH |
|---|---|---|
| 100 | 0 | 7.8 |
| 50 | 50 | 7 |
| 40 | 60 | 6.8 |
| 30 | 70 | 6.4 |
| 25 | 75 | 5.9 |
| 20 | 80 | 5.6 |
| 15 | 85 | 5.2 |
| 10 | 90 | 4.9 |

1.5 Albumin Elimination from Plasma Protein Samples

Additional experiments were done to determine at what percent of buffer B the cut-off should be taken in order to isolate albumin. One mL of the PBE 94 resin was pipetted into a 1.5 mL centrifuge tube. Then, 350 µL of a solution composed of 25% Buffer A and 75% Buffer B was added to the resin, the tube was vortexed for 30 seconds, and this was followed by centrifugation at 5000×g for 1 minute. The supernatant was discarded. This equilibration step was repeated twice. Following equilibration, 275 µg of plasma proteins was added to 350 µL of a solution composed of 25% Buffer A and 75% Buffer B. This mixture was then added to the resin, followed by vortexing for 30 seconds The tube was then centrifuged at 5000×g for 1 minute and the supernatant was recovered. The resin was washed three times with the same buffer (25% Buffer A, 75% Buffer B), with each iteration followed by vortexing for 30 seconds, centrifugation at 5000×g for 1 minute, and supernatant recovery. The supernatant from this phase contained proteins with a pI higher than that of albumin. The resin was then washed with 350 µL of a solution composed of 10% Buffer A and 90% Buffer B, vortexed for 30 seconds, and centrifuged at 5000×g for 1 minute. The supernatant from this phase, containing albumin, was also recovered. This step was repeated three times. Finally, four washes of 350 µL of a 0.1 M HCl solution were performed, and the same procedures were followed to recover the supernatant. The supernatant from this phase contained the acidic proteins. This separation yields 12 fractions.

1.6 SDS-Page Analysis of the Collected Fractions.

For this analysis, the fractions were vacuum dried, reconstituted with 30 µL of 50 mM Tris-HCl (pH 6.8), 2% SDS, 0.1% bromophenol blue, and 10% glycerol, and applied to a 10% polyacrylamide SDS gel. Gels were electrophoresed at 30 V for 30 minutes, then at 50 mA per gel for 45 minutes.

Figure 5A:
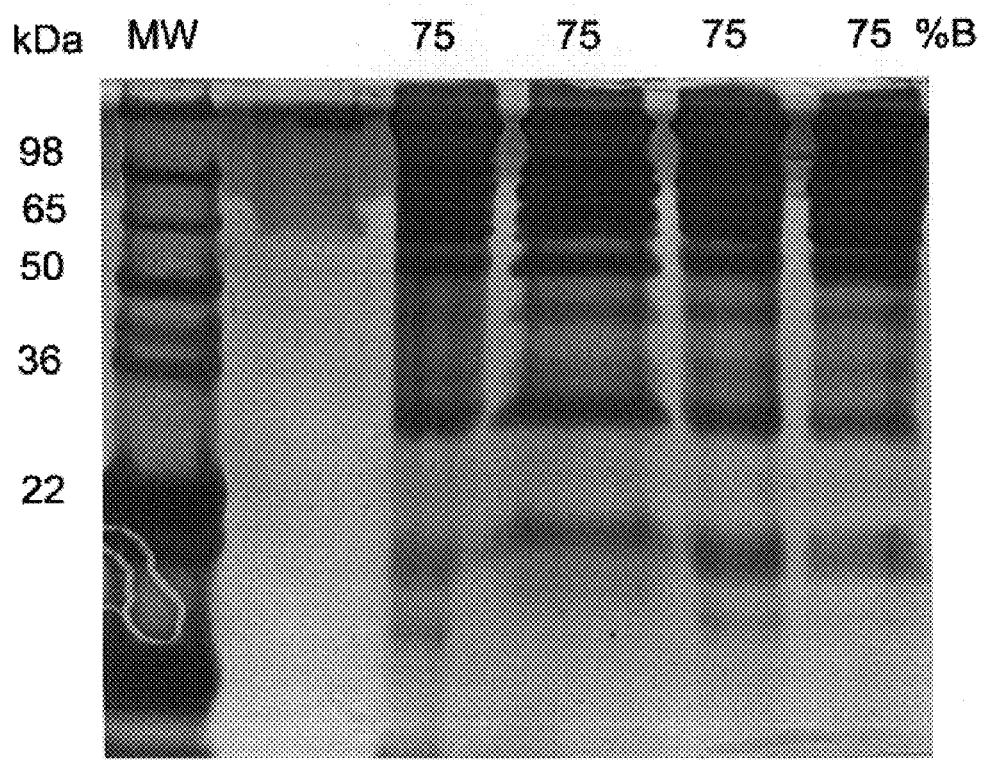
FIGS. 5A and 5B depict a 1 dimensional gel electrophoresis of the supernatant recovered after adding three different buffers (i.e., 75% buffer B, 90% buffer B, and 0.1 M HCl solution (pH 1)) to a plasma protein sample on PBE 94 resin, as described in Example 1. The proteins visualized on the gel are those that were solubilized. The percent of buffer B (v/v) is marked on the horizontal axis. The molecular weight (kDa) standards are marked on the vertical axis.
Figure 5B:
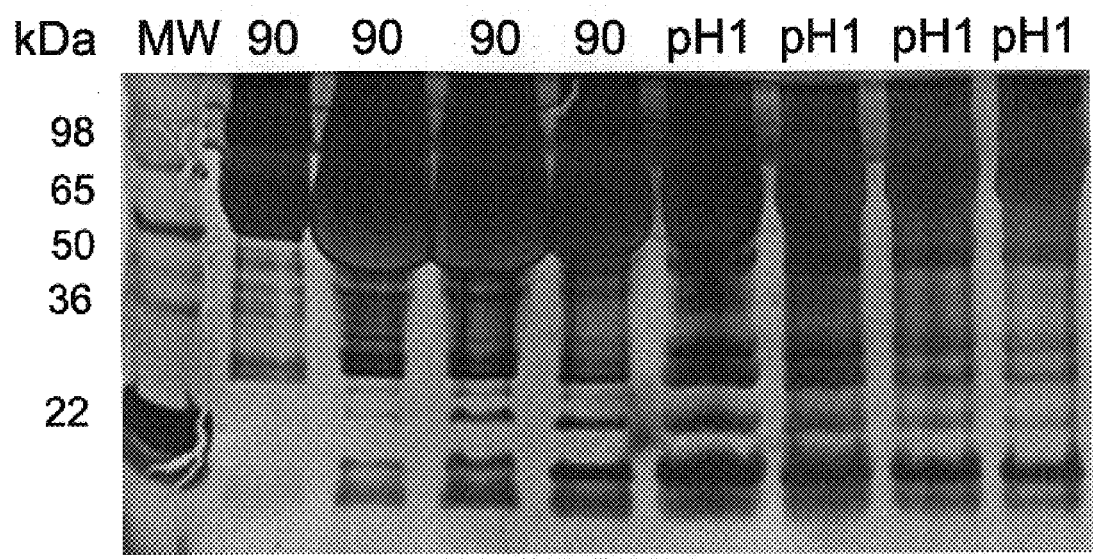
Figure 5C:
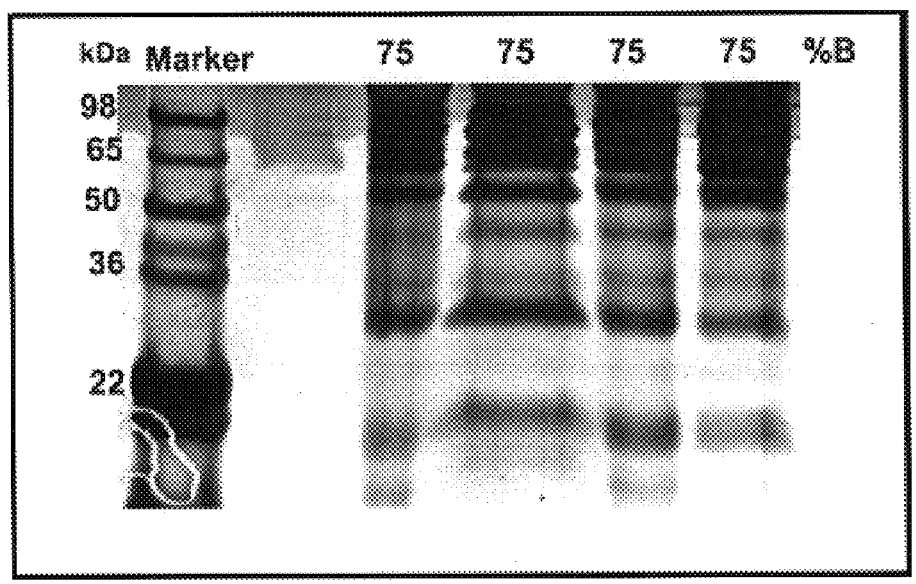
FIG. 5C and FIG. 5D depict the same gels as FIGS. 5A and 5B however.
Figure 5D:
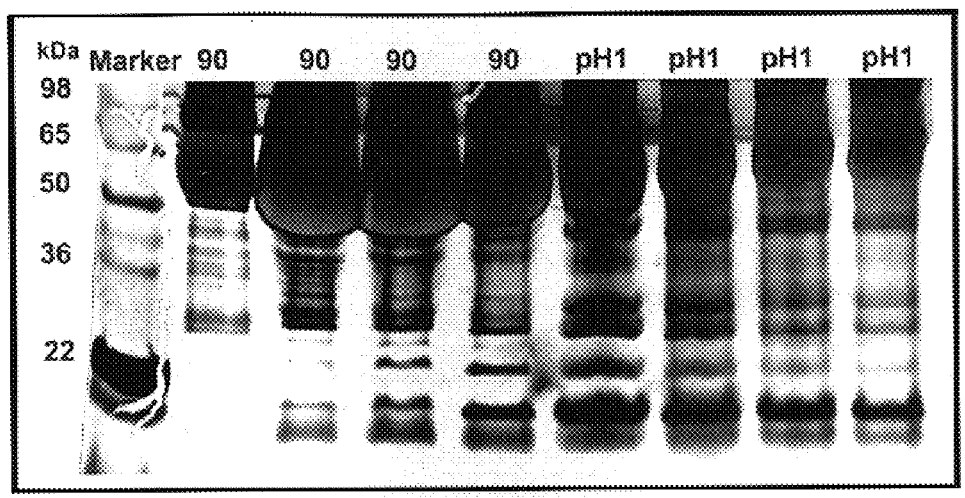

At 75% buffer B, no major 65 kDa bands appeared on the gel (FIGS. 5A and 5C). At 90% buffer B, dominant bands appear at 65 kDa (FIGS. 5B and 5D). At pH 1, a large band appeared at 65 kDa (FIGS. 5B and 5D).This band is thought to represent albumin or other proteins that have molecular masses comparable to that of albumin such as α1-antitrypsin and α1-antichymotrypsin.

1.7 Two-Dimensional Gel Electrophoresis.

For this analysis, fractions 1 to 4 and 9 to 12 were combined in one tube, while the four albumin-containing fractions (5 to 8) were combined in another. The two solutions were dried using a vacuum centrifuge and were then reconstituted in 185 µL of rehydration buffer consisting of 8 M urea, 50 mM dithiothreitol, 2% CHAPS, 0.2% Bio-lyte 3/10 Ampholyte, and 0.001% bromophenol blue. In addition to these two solutions 100 µg of the original human plasma protein sample was diluted with 185 µL of the same rehydration buffer. Protein concentrations in this example were determined using bicinchoninic acid assay (BCA®) (Pierce, Rockford, Ill.) with bovine serum albumin (BSA) standards according to the manufacturer's instructions. The concentration of proteins in human plasma and different fractions was determined using the standard curve generated by the absorbance at 562 nm.

Two runs of 2-DE were performed. The first run loaded 275 µg of protein and analyzed the untreated sample and treated sample (fractions 1 to 4 combined with fractions 9 to 12). The second run loaded 100 µg of protein and analyzed the untreated sample, treated sample (fractions 1 to 4 combined with fractions 9 to 12), and albumin fractions (5-8).

The IPG strips were rehydrated at 50 V for 16 hours at 20° C. using an immobilized pH Gradient (IPG) strip 1i cm long, pH 4 to 7. The proteins were focused at 250 V for 15 minutes; an 8000 V was then maintained for a total of 42,000 Vh per gel. The strips were then equilibrated for 10 minutes in 2.5 mL of a solution composed of 375 mM Tris-HCl pH 8.8, 6 M urea, 2% SDS and 2% dithiothreitol. After this first equilibration, the strip was equilibrated for another 10 minutes in 2.5 mL of a second equilibration buffer composed of 375 mM Tris-HCl pH 8.8, 6 M urea, and 2% SDS. The equilibrated IPG strips were washed with cathode buffer (0.1 M Tricine, 0.1 M Tris-HCl pH 8.2 and 0.1% SDS) and placed onto a 10% Tris-HCl Criterion® gel (Bio-Rad). The anode buffer consisted of 0.2 M Tris-HCl pH 8.9. Gels were electrophoresed at 20 mA/gel for 1 hour, then 100 mA/gel until the end of the separation.

All the gels were silver stained according to the following protocol: Gels were fixed in 50% methanol (v/v) and 12% acetic acid (v/v) for 2 hours, then washed 3 times in 50% ethanol (v/v). The duration of each wash was 20 minutes. Gels were then incubated in a 0.02% sodium thiosulfate solution (w/v) for 1 minute, followed by 4 one-minute washes in water. Gels were then placed in a solution composed of 0.2% silver nitrate (w/v) and 0.075% (v/v) formaldehyde for a period of 20 minutes, followed by 3 one-minute washes in water. Gels were then developed in a 6% sodium carbonate (w/v), 0.005% formaldehyde (v/v), and 0.004% sodium thiosulfate (w/v) solution until the protein bands were visualized. A 1% acetic acid solution was added to stop development of the gel.

Figure 6A:
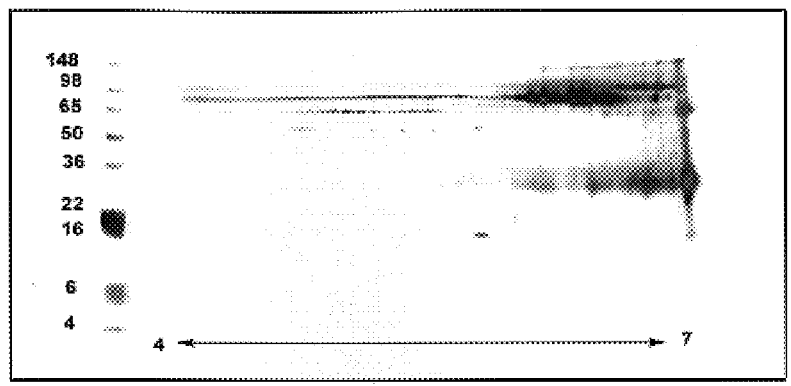
Figure 6B:
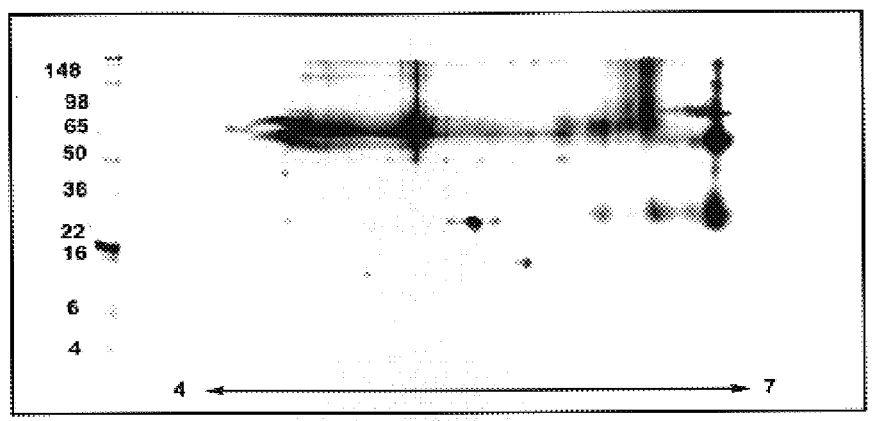

The 2-DE of the original plasma protein sample shows the presence of albumin and all the other proteins (FIG. 6A and 6D), and served as control for 2-DE of the remaining fractions. The 2-DE of the combined 8 fractions collected after the 75% B and pH washes shows little albumin presence (FIG. 6B and 6E). Large spots at acidic pI values close to 65 kDa represents al-acid glycoprotein, α1-antitrypsin, and α1-antichymotrypsin. The presence of proteins that have a pI similar to that of albumin was noticed as well. 2-DE of the combined 4 fractions collected after the 90% B washes shows mainly albumin (FIG. 6C), with traces of bands corresponding to other proteins in the original sample. The identification of the proteins was done by comparing their position on the gel to that of the Swiss2-DPAGE database (http://us.expasy.org/tools/).

Proteins with a pI value similar to albumin, such as antitrypsin (pI 5.37), antichymotrypsin (pI 5.33), transthyretin (pI 5.52), and al-acid glycoprotein (pi 5.65), were recovered after the separation procedure described here, in which Polybuffer Exchanger 94 resin was used to eliminate albumin from the human plasma protein sample. By adjusting the pH of the buffer-resin-human plasma sample mixture to a pH near the theoretical pI of albumin (5.92), by adding a 350 µL mixture consisting of 25% Buffer A and 75% Buffer B, all of the proteins that have a pI higher than that of albumin will be positively charged, and therefore, will remain in solution. Proteins that have a pI equal or close to that of albumin will be zero-charged, and will therefore precipitate. Some albumin molecules will be zero-charged, others with different glycation states will be slightly positively or negatively charged, depending on their pI, and will possibly precipitate during centrifugation due to their high molecular mass and low charge density. Proteins that have a pI lower than that of albumin will be negatively charged, and will therefore bind to the resin. The centrifugation allows for the formation of 2 layers: the bottom layer is the resin with the proteins bound to it, in addition to the precipitated albumin, and the top layer is the solution containing free proteins. This supernatant is recovered.

After this first step, the pH of the buffer-resin- human plasma sample is adjusted to a value that is approximately one unit lower than the pI of albumin (pH=4.7) by adding 350 µL of a mixture composed of 10% Buffer A and 90% Buffer B. Albumin, as well as proteins that share the same pI, will be positively charged and will therefore be soluble in the solution. Centrifugation then allows for the isolation of the supernatant solution containing primarily albumin. The last step is the addition of 350 µL of 0.1 M HCl solution. All acidic proteins bound to the resin will then be released and recovered by centrifugation. The recovery of several proteins or fragments that are in the same pI range as albumin is thought to be due to their higher solubility in the solution than albumin when their net charge is close to zero. When the pH is adjusted to a pI that is approximately equal to the theoretical pI of albumin, the net charge of some albumin molecules of certain glycation states, in addition to these recovered proteins and fragments, will be close to zero, and are therefore theoretically insoluble. The centrifugation at 5000×g results in the precipitation of albumin but not of some smaller proteins and fragments, because these molecules have smaller sizes and may be soluble in the relatively high ionic strength of the buffers (approximately 50 mM).

Figure 6C:
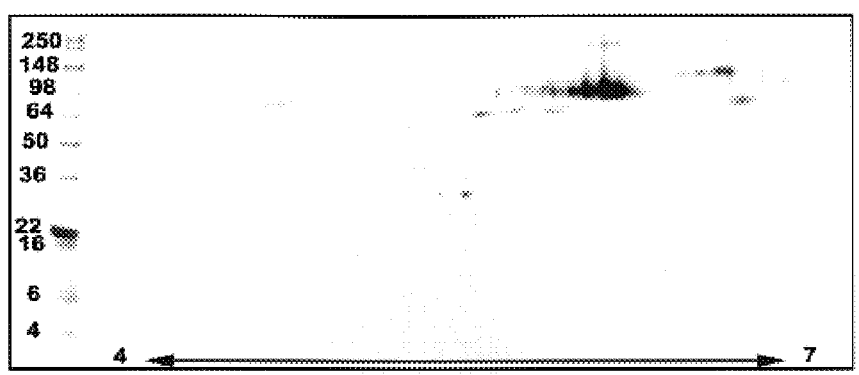

A quantitative analysis of protein concentration showed that 27.63 µg of proteins were present in the mixture containing fractions 1 to 4 and 9 to 12 (FIG. 6B), and 68.36 µg in the mixture containing fractions 5 to 8 (FIG. 6C). This represents a protein recovery of 96%.

Imaging Analysis

The number of individual spots on the gels was determined using ImageMaster 2D Platinum (Amersham Biosciences Corporation, Uppsala, Sweden). The parameters used were: Smooth 5, Min. Area 5, Saliency 1.0000.

ImageMaster 2D Platinum detected 62 spots in the 2-DE of total plasma protein versus 215 spots for the 2-DE of albumin-depleted plasma which represents a 3.4-fold increase in the number of spots detected.

1.8 Western Blotting

Matrix metalloproteinases (MMPs) are a group of zinc-containing enzymes that can collectively degrade all components of extracellular matrices (ECM) and some cell surface proteins. MMPs participate in tumor invasion and metastasis by hydrolyzing the basement membrane and other proteins, allowing the cancer cells to gain access to blood and lymph vessels. The detection of MMPs in the serum samples is important since studies on MMP-2 and MMP-9 showed that increased expression of these enzymes in the serum of prostate cancer patients detected using enzyme-linked immunosorbent assay (ELISA) is associated with advanced tumor stages. MMP-26, is the smallest member of the MMP family and is also known as endometase/matrilysin-2.

The ability of batch anion exchange prefractionation to remove albumin and increase detection of MMP-26 in human plasma samples was analyzed. Human plasma sample was diluted with a buffer composed of 25% buffer A and 75% buffer B to a volume of 400 µL and was added to 1 mL of the PBE94 resin that was previously washed with the same buffer composition. The mixture was then vortex mixed and centrifuged. The supernatant was collected. The resin was then washed three times with 350 µL of the same buffer compositions vortex mixed and centrifuged as described above. After performing BCA assay on this fraction, 10 µg of proteins were reconstituted with 15 µL of SDS-PAGE buffer and loaded on a 10% polyacrylamide gel against 10 µg of total plasma proteins as control. The gel was electrophoresed at 30 V for 30 minutes, then 50 mA until the end of the separation. Proteins contained within the gel were then electroblotted onto a nitrocellulose membrane (50 V for 50 minutes). Western blot analysis for MMP-26 was accomplished utilizing a 1 µg/mL dilution of rabbit anti-MMP-26 followed by incubation with horse radish peroxidase-conjugated anti-rabbit antibody. Visualization of the bands was then accomplished by the addition of a 1 to 1 ratio of Super Signal West Pico-Stable Peroxidase Solution and Luminol/Enhancer Solution (Pierce, Rockford, Ill.) and by developing the chemiluminescent signal on a Kodak film in the dark using Kodak Scientific Imaging Film (Kodak cat. 1651496), Fixer and Replenisher/Developer and Replenisher (Kodak cat. 1901859) according to the manufacturer's instructions.

Figure 7:
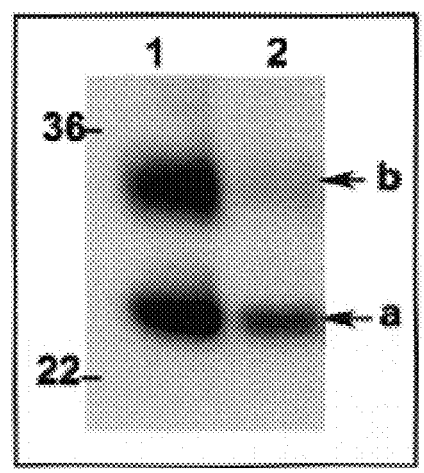
FIG. 7 depicts the Western blot of MMP-26 as described in Example 1. Western blotting of MMP-26 in human patient sera contained in 10 µg of an albumin-depleted human plasma sample (lane 1) and 10 µg of total human plasma (lane 2). Numbers on the left indicate molecular masses in kDa. Band a represents the glycosylated active form of MMP-26; band b represents the glycosylated latent form of MMP-26.

MMP-26 has a theoretical pI of 6.2, a molecular weight of 19 kDa for the active form and 26 kDa for the latent form, and has 3 potential glycosylation sites. Two bands were visualized between 22 and 36 kDa (FIG. 7) in the albumin-depleted sample corresponding to the glycosylated latent and active forms of MMP-26. The elimination of not only albumin but also all the other proteins that have pI values below 6 allowed increased loading of human plasma proteins that is crucial for enhancing the detection of low-abundance proteins like MMP-26.

Example 2

Fractionation of Cancer Serum Sample

Prostate-specific antigen (PSA) is an established serum marker for the diagnosis and management of prostate caner. The proteolytic activity of PSA is inhibited by antichymotrypsin (ACT). PSA binds covalently to ACT and forms a complex (PSA-ACT). PSA-ACT is the major form of PSA present in human serum. The ratio of free PSA (FPSA) to PSA-ACT is of major clinical significance as it allows for the best clinical performance for prostate cancer detection.

The ability of batch anion exchange prefractionation to remove albumin and increase sensitivity of serum (PSA) analysis was compared to commercially available albumin purification methods based on, Cibacron Blue F3GA and albumin antibodies. Prostate cancer serum samples were provided by Dr. Kenneth A. lczkowski, University of Florida, College of Medicine, Department of Pathology, Immunology and Laboratory Medicine, Gainesville, Fla.

2.1 Determination of Protein Concentrations

Protein concentrations in serum samples and fractions collected was determined using bicinchoninic acid assay (BCA®) (Pierce, Rockford, Ill.) with bovine serum albumin (BSA) standards according to the manufacturer's instructions. The concentration of proteins in human serum and different fractions was determined using the standard curve generated by the absorbance at 562 nm.

2.2 Albumin Elimination Using Commercially-Available Kits

SwellGel® Blue Albumin Removal Kit (Pierce, Rockford, Ill.) and ProteoSeek™ Antibody-Based Albumin/IgG Removal Kit (Pierce, Rockford, Ill.) were used according to the manufacturer's instructions. The albumin bound fraction was eluted by washing the SweliGel® resin with 0.25 M sodium thiocyanate 0.02 M sodium phosphate and the ProteoSeek™ resin with boiling deionized water.

2.3 Serum Prefractionation

One mL of the PBE 94 resin was pipetted into a 1.5 mL centrifuge tube. Then, 350 µL of a solution composed of 25% Buffer A (from example 1) and 75% Buffer B (from example 1) was added to the resin, the tube was vortexed for 30 seconds, and this was followed by centrifugation at 5000×g for 30 seconds The supernatant was discarded. This equilibration step was repeated twice. Following equilibration, 275 µg of serum proteins were diluted with 350 µL of a buffer composed of 5 M urea, 2 M thiourea, 1% octylglucopyranoside (OG), 0.25% w/v Biolyte 3-10 ampholyte, 12.5% water saturated isobutanol, 10% isopropanol, 5% glycerol, and 50 mM dithiothreitol (DTT) and added to the resin followed by vortexing for 30 seconds The tube was then centrifuged at 5000×g for 30 seconds and the supernatant was recovered. The resin was washed three times with the same buffer (25% Buffer A, 75% Buffer B), with each iteration followed by vortexing for 30 seconds, centrifugation at 5000×g for 30 seconds, and supernatant recovery. The supernatant from this phase contained proteins with a pI higher than that of albumin. The resin was then washed with 350 µL of a solution composed of 10% Buffer A and 90% Buffer B, vortexed for 30 seconds, and centrifuged at 5000×g for 30 seconds The supernatant from this phase, containing albumin, was also recovered. This step was repeated three times. Finally, four washes of 350 µL of a 0.1 M HCl solution were performed, and the same procedures were followed to recover the supernatant. The supernatant from this phase contained the acidic proteins. This separation yields 12 fractions.

2.4 Western Blotting

After performing BCA assay, 10 µg of proteins from each fraction collected were reconstituted with 15 µL of SDS-PAGE buffer and loaded on a 10% polyacrylamide gel. The gel was electrophoresed at 30 V for 30 minutes, then 50 mA until the end of the separation. Proteins contained within the gel were then electroblotted onto a nitrocellulose membrane (50 V for 50 minutes). Western blot analysis for PSA was accomplished utilizing a 1 µg/mL dilution of monoclonal mouse anti-PSA (Santa Cruz Biotechnology, Santa Cruz, Calif.) followed by incubation with horse radish peroxidase-conjugated anti-mouse antibody. Visualization of the bands was then accomplished by the addition of a 1 to 1 ratio of Super Signal West Pico-Stable Peroxidase Solution and Luminol/Enhancer Solution (Pierce, Rockford, Ill.) and by developing the chemiluminescent signal on a Kodak film in the dark using Kodak Scientific Imaging Film (Kodak cat. 1651496), Fixer and Replenisher/Developer and Replenisher (Kodak cat. 1901859) according to the manufacturer's instructions.

Figure 8:
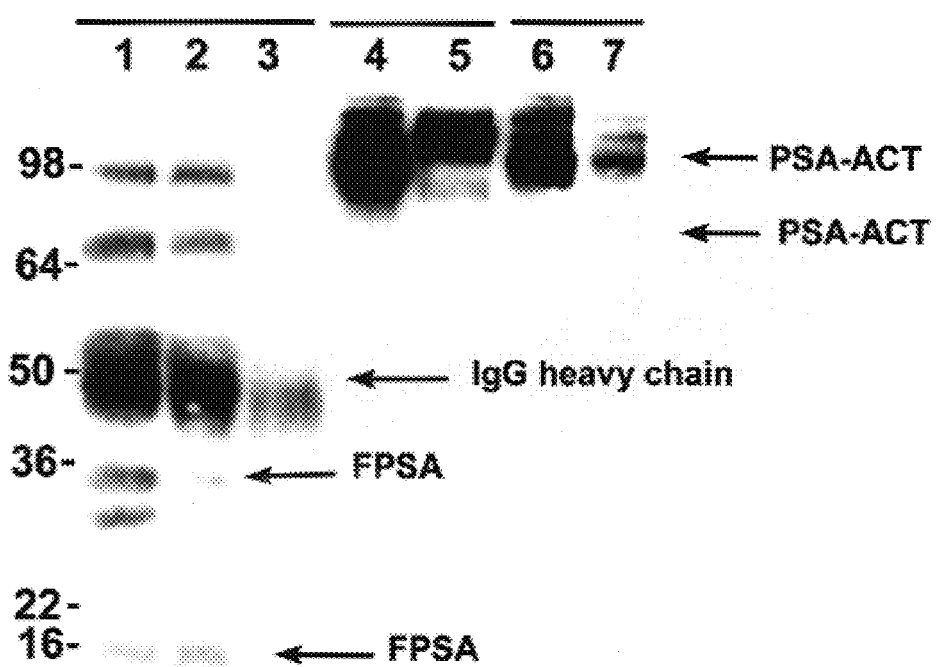
FIG. 8 depicts the Western blot of prostate-specific antigen (PSA) described in Example 2. Western blotting of PSA in a prostate cancer human patient serum is shown. Lane 1,10 µg of proteins with pIs higher than that of albumin; lane 2,10 µg of proteins with pIs similar to that of albumin; lane 3,10 µg of proteins with pIs lower than that of albumin; lane 4, 10 µg of albumin-depleted serum using Cibacron blue F3GA; lane 5, 10 µg of the albumin fraction recovered after Cibacron blue F3GA treatment; lane 6,10 µg of albumin and IgG-depleted serum sample using albumin antibody-conjugated resin; and lane 7,10 µg of the albumin and IgG fraction recovered from the antibody-conjugated resin. Numbers on the left indicate molecular masses in kDa.
Figure 9:
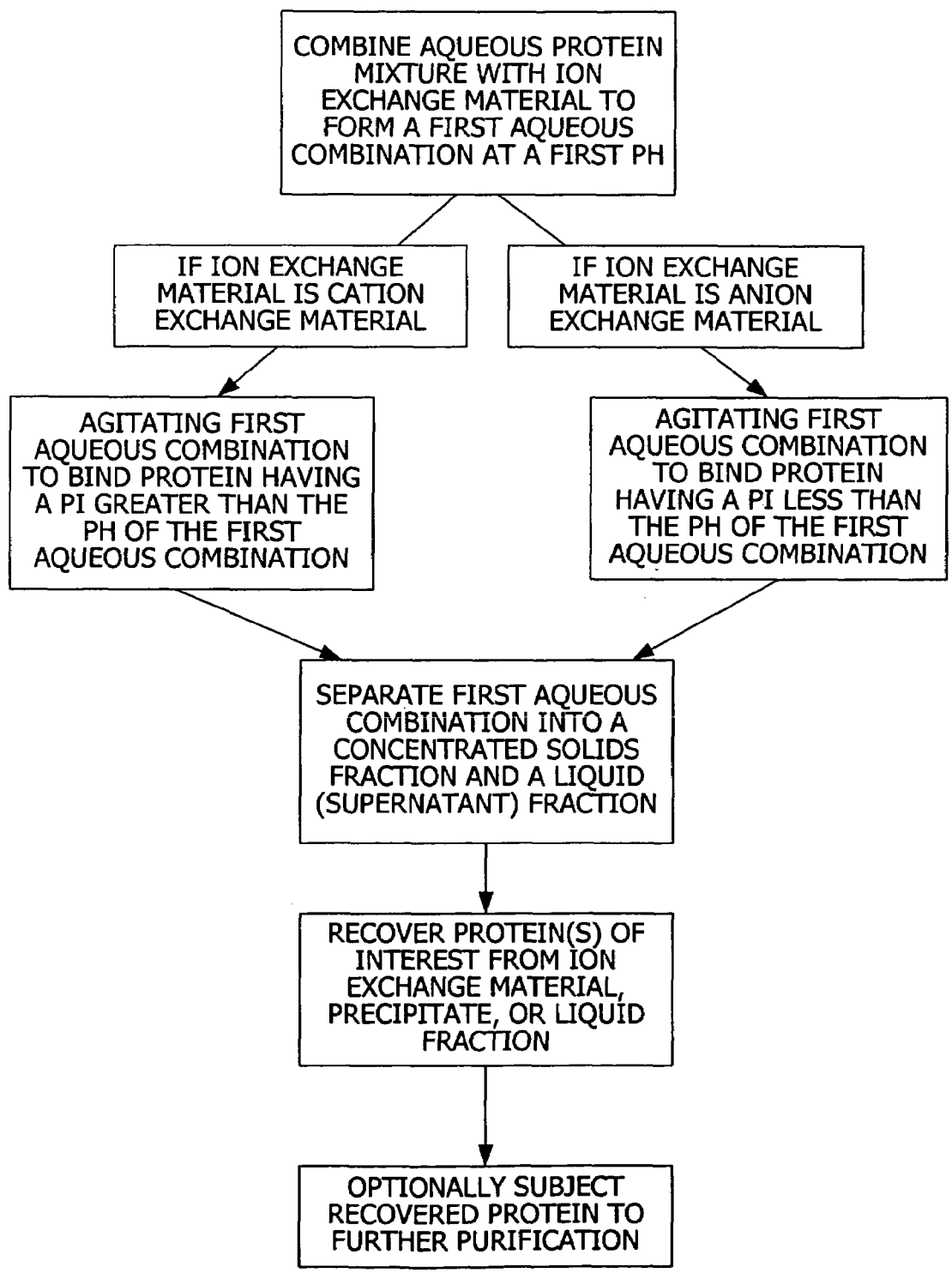
FIG. 9 is a schematic series of steps comprising one embodiment of the present invention.

PSA bands are usually detected at a molecular mass of 13 to 34 kDa and have a pI of 8-8.8 44, 45. PSA-ACT complex is detected at a molecular mass of 96 kDa and have a pI of 6.5 to 7 46. PSA-ACT doublet which is the major form of PSA in the serum 37-42 was detected around 96 kDa in the first 2 fractions collected after batch anion exchange chromatography as well as in the albumin-depleted serum and the albumin fractions collected after using the 2 albumin elimination kits (FIG. 8). FPSA (14-34 kDa) which is the low-abundant form of PSA was detected in the first 2 fractions collected after batch anion exchange chromatography but not in the fractions collected after albumin elimination. The large band at 50 kDa represents IgG heavy chain that is immunoreactive with the secondary antibody used. Batch anion exchange prefractionation of the serum proteins resulted in a better protein denaturation and resolution since the serum sample was diluted with a buffer that contains 5 M urea, 2 M thiourea, 1% octylglucopyranoside (OG), 0.25% w/v Biolyte 3-10 ampholyte, 12.5% water saturated isobutanol, 10% isopropanol, 5% glycerol, and 50 mM dithiothreitol (DTT) prior to prefractionation.

What is claimed is:

1. A method for separating albumin from a sample comprising albumin and other proteins, the method comprising:
    combining the sample with an ion exchange material to form a first aqueous combination, the pH of the first aqueous combination being (i) less than the pI of a first fraction of the proteins in the first aqueous combination, (ii) greater than the pI of a second fraction of the proteins in the first aqueous combination, and (iii) a pH at which albumin precipitates from the first aqueous combination;
    agitating the first aqueous combination to induce the albumin to precipitate and to cause protein comprised by one of said first and second fractions to bind to the ion exchange material; and
    separating the ion exchange material from the agitated aqueous combination.

2. The method of claim 1 wherein said agitating step results in turbulent flow of the sample over the anion exchange material.

3. The method of claim 1 wherein the ion exchange material is in the form of a particulate ion exchange resin, the first aqueous combination is an aqueous dispersion formed by combining the sample with the particulate ion exchange material, and said separating step comprises centrifuging the agitated first aqueous dispersion to cause the first aqueous dispersion to stratify into a first concentrated solids fraction and a first supernatant, the first concentrated solids fraction comprising the ion exchange resin, its bound proteins, and precipitate.

4. The method of claim 3 wherein the ion exchange material is particulate anion exchange resin and the pH of the first aqueous dispersion is about 5.9.

5. The method of claim 4, the method further comprising:
    forming a second aqueous dispersion wherein the second aqueous dispersion comprises the separated first concentrated solids fraction and has a pH at which (i) albumin in the second aqueous dispersion dissolves into the second aqueous dispersion, and (ii) at least a fraction of protein bound to the anion exchange resin of the first concentrated solids fraction remains bound to the anion exchange resin;
    agitating the second aqueous dispersion;
    centrifuging the agitated second aqueous dispersion to form a second supernatant fraction and a second concentrated solids fraction, the second concentrated solids fraction comprising the anion exchange resin and its bound proteins; and
    separating the second supernatant from the second concentrated solids fraction.

6. The method of claim 5 wherein the second aqueous dispersion has a pH of less than about 5.9.

7. The method of claim 5 wherein the albumin is dissolved into the second aqueous dispersion by decreasing the pH of the second aqueous dispersion in a stepwise manner, and wherein each pH adjustment is followed by agitating the adjusted mixture, centrifuging the agitated adjusted mixture to form a supernatant fraction and a concentrated solids fraction comprising the anion exchange resin and its bound proteins, and separating the supernatant from the concentrated solids fraction.

8. The method of claim 5, the method further comprising:
forming a third aqueous dispersion, the third aqueous dispersion comprising the separated second concentrated solids fraction at a pH at which all proteins are released from the anion exchange resin;
agitating the third aqueous dispersion;
centrifuging the agitated third aqueous dispersion to form a third supernatant fraction and a third concentrated solids fraction, the third concentrated solids fraction comprising the anion exchange resin; and
separating the third supernatant from the third concentrated solids fraction.

9. The method of claim 8 wherein the pH of the third aqueous dispersion is about 1.0.

10. The method of claim 5 wherein the second aqueous dispersion has a pH of about 4.9.

11. The method of claim 5, the method further comprising
forming a third aqueous dispersion, the third aqueous dispersion comprising the separated second concentrated solids fraction at a pH at which (i) at least a fraction of protein bound to the anion exchange resin of the second concentrated solids fraction is released from the anion exchange resin, and (ii) the proteins are not denatured;
agitating the third aqueous dispersion;
centrifuging the agitated third aqueous dispersion to form a third supernatant fraction and a third concentrated solids fraction, the third concentrated solids fraction comprising the anion exchange resin; and
separating the third supernatant from the third concentrated solids fraction.

12. The method of claim 11 wherein the third aqueous dispersion has a pH of less than about 4.9.

13. The method of claim 11 wherein proteins are released from the anion exchange resin by decreasing the pH of the third aqueous dispersion in a stepwise manner, and wherein each pH adjustment is followed by agitating the adjusted mixture, centrifuging the agitated adjusted mixture to form a supernatant fraction and a concentrated solids fraction comprising the anion exchange resin and its bound proteins, and separating the supernatant from the concentrated solids fraction.

14. The method of claim 11 further comprising:
forming a fourth aqueous dispersion, the fourth aqueous dispersion comprising the separated third concentrated solids fraction at a pH at which all proteins are released from the anion exchange resin;
agitating the fourth aqueous dispersion;
centrifuging the agitated fourth aqueous dispersion to form a fourth supernatant fraction and a fourth concentrated solids fraction, the fourth concentrated solids fraction comprising the anion exchange resin; and
separating the fourth supernatant from the fourth concentrated solids fraction.

15. The method of claim 14 wherein the pH of the fourth aqueous dispersion is about 1.0.

16. The method of claim 4, the method further comprising:
forming a second aqueous dispersion, the second aqueous dispersion comprising the separated first concentrated solids fraction at a pH at which (i) all proteins are released from the anion exchange resin, and (ii) all precipitated albumin and proteins dissolve into the second aqueous dispersion;
agitating the second aqueous dispersion;
centrifuging the agitated second aqueous dispersion to form a second supernatant fraction and a second concentrated solids fraction, the second concentrated solids fraction comprising the anion exchange resin; and
separating the second supernatant from the second concentrated solids fraction.

17. The method of claim 16 wherein the pH of the second aqueous dispersion is about 1.0.

18. The method of claim 3 wherein the ion exchange resin is equilibrated to a pH of about 5.9 prior to forming the first aqueous dispersion.

19. The method of claim 1 wherein the agitated first aqueous dispersion is centrifuged at a force of about 5000×g.

20. The method of claim 1 wherein the sample is selected from the group consisting of plasma, amniotic fluid, seminal fluid, and cerebral spinal fluid.

21. The method of claim 3 wherein the ion exchange material is particulate cation exchange resin and the pH of the first aqueous dispersion is about 5.9.

22. The method of claim 21, the method further comprising:
forming a second aqueous dispersion wherein the second aqueous dispersion comprises the separated first concentrated solids fraction and has a pH at which (i) albumin in the second aqueous dispersion dissolves into the second aqueous dispersion, and (ii) at least a fraction of protein bound to the cation exchange resin of the first concentrated solids fraction remains bound to the cation exchange resin;
agitating the second aqueous dispersion;
centrifuging the agitated second aqueous dispersion to form a second supernatant fraction and a second concentrated solids fraction, the second concentrated solids fraction comprising the cation exchange resin; and
separating the second supernatant from the second concentrated solids fraction.

23. The method of claim 22 wherein the second aqueous dispersion has a pH of greater than about 5.9.

24. The method of claim 22 wherein the albumin is dissolved into the second aqueous dispersion by raising the pH of the second aqueous dispersion in a stepwise manner, and wherein each pH adjustment is followed by agitating the adjusted mixture, centrifuging the agitated adjusted mixture to form a supernatant fraction and a concentrated solids fraction comprising the cation exchange resin, and separating the supernatant from the concentrated solids fraction.

25. The method of claim 22, the method further comprising
forming a third aqueous dispersion, the third aqueous dispersion comprising the separated second concentrated solids fraction at a pH at which all proteins are released from the cation exchange resin;
agitating the third aqueous dispersion;
centrifuging the agitated third aqueous dispersion to form a third supernatant fraction and a third concentrated solids fraction, the third concentrated solids fraction comprising the cation exchange resin; and
separating the third supernatant from the third concentrated solids fraction.

26. The method of claim 25 wherein the pH of the third aqueous dispersion is about 14.0.

27. The method of claim 22 wherein the second aqueous dispersion has a pH of about 6.9.

28. The method of claim 22, the method further comprising:
forming a third aqueous dispersion, the third aqueous dispersion comprising the separated second concentrated solids fraction at a pH at which (i) at least a fraction of protein bound to the cation exchange resin of the second concentrated solids fraction is released from the cation exchange resin, and (ii) the proteins are not denatured;
agitating the third aqueous dispersion;
centrifuging the agitated third aqueous dispersion to form a third supernatant fraction and a third concentrated solids fraction, the third concentrated solids fraction comprising the cation exchange resin; and
separating the third supernatant from the third concentrated solids fraction.

29. The method of claim 28 wherein the third aqueous dispersion has a pH of greater than about 6.9.

30. The method of claim 28 wherein proteins are released from the cation exchange resin by raising the pH of the third aqueous dispersion in a stepwise manner, and wherein each pH adjustment is followed by agitating the adjusted mixture, centrifuging the agitated adjusted mixture to form a supernatant fraction and a concentrated solids fraction comprising the cation exchange resin, and separating the supernatant from the concentrated solids fraction.

31. The method of claim 28, the method further comprising
forming a fourth aqueous dispersion, the fourth aqueous dispersion comprising the separated third concentrated solids fraction at a pH at which all proteins are released from the cation exchange resin;
agitating the fourth aqueous dispersion;
centrifuging the agitated fourth aqueous dispersion to form a fourth supernatant fraction and a fourth concentrated solids fraction, the fourth concentrated solids fraction comprising the cation exchange resin; and
separating the fourth supernatant from the fourth concentrated solids fraction.

32. The method of claim 31 wherein the pH of the fourth aqueous dispersion is about 14.0.

33. The method of claim 21, the method further comprising
forming a second aqueous dispersion, the second aqueous dispersion comprising the separated first concentrated solids fraction at a pH at which (i) all proteins are released from the cation exchange resin, and (ii) all precipitated albumin and proteins dissolve into the second aqueous dispersion;
agitating the second aqueous dispersion;
centrifuging the agitated second aqueous dispersion to form a second supernatant fraction and a second concentrated solids fraction, the second concentrated solids fraction comprising the cation exchange resin; and
separating the second supernatant from the second concentrated solids fraction.

34. The method of claim 33 wherein the pH of the second aqueous dispersion is about 14.0.

35. The method of claim 1 wherein the ion exchange material is a combination of anion exchange and cation exchange material, the anion exchange material and cation exchange material being kept physically separate to minimize contact between the two, and, during the agitating step, protein having a pI less than the pH of the first aqueous combination binds to the anion exchange material whereas protein having a pI greater than the pH of the first aqueous combination binds to the cation exchange material.

* * * * *